(12) United States Patent
Mourich et al.

(10) Patent No.: US 8,592,386 B2
(45) Date of Patent: Nov. 26, 2013

(54) ANTISENSE COMPOSITIONS AND METHODS FOR MODULATING CONTACT HYPERSENSITIVITY OR CONTACT DERMATITIS

(75) Inventors: Dan V. Mourich, Albany, OR (US); Nikki B. Marshall, Corvallis, OR (US); Patrick L. Iversen, Corvallis, OR (US)

(73) Assignee: Sarepta Therapeutics, Inc., Corvallis, OR (US)

( * ) Notice: Subject to any disclaimer, the term of this patent is extended or adjusted under 35 U.S.C. 154(b) by 365 days.

(21) Appl. No.: 12/641,159

(22) Filed: Dec. 17, 2009

(65) Prior Publication Data

US 2010/0184670 A1 Jul. 22, 2010

Related U.S. Application Data

(60) Provisional application No. 61/138,460, filed on Dec. 17, 2008.

(51) Int. Cl.
*A61K 31/70* (2006.01)
*C07H 21/04* (2006.01)

(52) U.S. Cl.
USPC .................................. 514/44 A; 536/24.5

(58) Field of Classification Search
USPC .................................. 514/44 A; 536/24.5
See application file for complete search history.

(56) References Cited

U.S. PATENT DOCUMENTS

| | | | |
|---|---|---|---|
| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton et al. |
| 5,214,134 A | 5/1993 | Weis et al. |
| 5,216,141 A | 6/1993 | Benner |
| 5,217,866 A | 6/1993 | Summerton et al. |
| 5,235,033 A | 8/1993 | Summerton et al. |
| 5,264,562 A | 11/1993 | Matteucci |
| 5,264,564 A | 11/1993 | Matteucci |
| 5,405,938 A | 4/1995 | Summerton et al. |
| 5,434,257 A | 7/1995 | Matteucci et al. |
| 5,466,677 A | 11/1995 | Baxter et al. |
| 5,470,967 A | 11/1995 | Huie et al. |
| 5,489,677 A | 2/1996 | Sanghvi et al. |
| 5,506,337 A | 4/1996 | Summerton et al. |
| 5,521,063 A | 5/1996 | Summerton et al. |
| 5,539,082 A | 7/1996 | Nielsen et al. |
| 5,541,307 A | 7/1996 | Cook et al. |
| 5,561,225 A | 10/1996 | Maddry et al. |
| 5,576,302 A | 11/1996 | Cook et al. |
| 5,580,767 A | 12/1996 | Cowsert et al. |
| 5,596,086 A | 1/1997 | Matteucci et al. |
| 5,602,240 A | 2/1997 | De Mesmaeker et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,633,360 A | 5/1997 | Bischofberger et al. |
| 5,663,312 A | 9/1997 | Chaturvedula |
| 5,677,437 A | 10/1997 | Teng et al. |
| 5,677,439 A | 10/1997 | Weis et al. |
| 5,698,685 A | 12/1997 | Summerton et al. |
| 5,702,891 A | 12/1997 | Kolberg et al. |
| 5,714,331 A | 2/1998 | Buchardt et al. |
| 5,719,262 A | 2/1998 | Buchardt et al. |
| 5,733,781 A | 3/1998 | Ryder et al. |
| 5,734,039 A | 3/1998 | Calabretta et al. |
| 5,801,154 A | 9/1998 | Baracchini et al. |
| 5,849,727 A | 12/1998 | Porter et al. |
| 5,892,023 A | 4/1999 | Pirotzky et al. |
| 5,955,318 A | 9/1999 | Simons et al. |
| 6,060,456 A | 5/2000 | Arnold et al. |
| 6,133,246 A | 10/2000 | McKay et al. |
| 6,174,868 B1 | 1/2001 | Anderson et al. |
| 6,210,892 B1 | 4/2001 | Bennett et al. |
| 6,228,579 B1 | 5/2001 | Zyskind et al. |
| 6,239,265 B1 | 5/2001 | Cook |
| 6,306,993 B1 | 10/2001 | Rothbard et al. |
| 6,365,351 B1 | 4/2002 | Iversen |
| 6,495,663 B1 | 12/2002 | Rothbard |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez et al. |
| 7,049,431 B2 | 5/2006 | Iversen et al. |
| 7,094,765 B1 | 8/2006 | Iversen et al. |

(Continued)

FOREIGN PATENT DOCUMENTS

EP 0 403 333 A2 12/1990
FR 2647809 A1 12/1990

(Continued)

OTHER PUBLICATIONS

Arora et al., Pharmaceutical Research (2002), vol. 19, No. 10, pp. 1465-1470.*
Agrawal et al., "Antisense oligonucleotides: towards clinical trials," *TIBTECH* 14:376-387, 1996.
Agrawal et al., "Antisense Therapeutics: Is it as Simple as complementary Base Recognition?," *Molecular Medicine Today* 6:72-81, 2000.
Agrawal et al., "Oligodeoxynucleotide phosphoramidates and phosphorothioates as inhibitors of human immunodeficiency virus," *Proc Natl Acad Sci USA* 85(19):7079-7083, 1988.
Agrawal et al., "Site-specific excision from RNA by RNase H and Mixed-phosphate-backbone oligonucleotides," *Proc Natl Acad Sci USA* 87(4):1401-1405, 1990.
Akhtar et al., "Interactions of antisense DNA oligonucleotide analogs with phospholipid membranes (liposomes)," *Nucleic Acids Res* 19(20):5551-5559, 1991.

(Continued)

*Primary Examiner* — Jon E Angell
(74) *Attorney, Agent, or Firm* — Seed IP Law Group PLLC

(57) ABSTRACT

Provided are methods and compositions, including topical compositions, for inducing tolerance to a sensitizing agent known to provoke contact hypersensitivity in a subject. Included are methods of topically applying to the subject an effective amount of an antisense composition targeting the start site or splice site of a CFLAR mRNA.

14 Claims, 9 Drawing Sheets

(56) References Cited

U.S. PATENT DOCUMENTS

| | | | |
|---|---|---|---|
| 7,115,374 | B2 | 10/2006 | Linnen et al. |
| 7,468,418 | B2 | 12/2008 | Iversen et al. |
| 8,008,469 | B2 | 8/2011 | Mourich et al. |
| 2002/0049173 | A1 | 4/2002 | Bennett et al. |
| 2002/0127198 | A1 | 9/2002 | Rothbard et al. |
| 2003/0166588 | A1 | 9/2003 | Iversen et al. |
| 2003/0171335 | A1 | 9/2003 | Stein et al. |
| 2003/0224353 | A1 | 12/2003 | Stein et al. |
| 2004/0254137 | A1 | 12/2004 | Ackermann et al. |
| 2004/0259108 | A1 | 12/2004 | Linnen et al. |
| 2004/0265879 | A1 | 12/2004 | Iversen et al. |
| 2005/0176661 | A1 | 8/2005 | Vaillant et al. |
| 2005/0203041 | A1* | 9/2005 | Mourich et al. ............. 514/44 |
| 2005/0234002 | A1 | 10/2005 | Mourich et al. |
| 2006/0135454 | A1 | 6/2006 | Kandimalla et al. |
| 2006/0149046 | A1 | 7/2006 | Arar |
| 2006/0269911 | A1 | 11/2006 | Iversen et al. |
| 2006/0276425 | A1 | 12/2006 | Mourich et al. |
| 2007/0122821 | A1 | 5/2007 | Iversen et al. |
| 2008/0027214 | A1 | 1/2008 | Kandimalla et al. |
| 2009/0082547 | A1 | 3/2009 | Iversen et al. |
| 2009/0088562 | A1 | 4/2009 | Weller et al. |
| 2009/0099066 | A1 | 4/2009 | Moulton et al. |
| 2009/0110689 | A1 | 4/2009 | Mourich et al. |
| 2009/0149404 | A1 | 6/2009 | Kaneko et al. |
| 2009/0246221 | A1 | 10/2009 | Mourich et al. |
| 2010/0184670 | A1 | 7/2010 | Mourich et al. |

FOREIGN PATENT DOCUMENTS

| | | |
|---|---|---|
| WO | 90/07936 A1 | 7/1990 |
| WO | 91/05864 A1 | 5/1991 |
| WO | 95/05851 A1 | 3/1995 |
| WO | 00/71706 A1 | 11/2000 |
| WO | 01/72765 A1 | 10/2001 |
| WO | 02/071062 A2 | 9/2002 |
| WO | 2005/030799 A1 | 4/2005 |
| WO | 2007/046087 A2 | 4/2007 |
| WO | 2009/086469 A2 | 7/2009 |
| WO | 2010/080554 A1 | 7/2010 |

OTHER PUBLICATIONS

Anderson et al., "Distribution of equilibrative, nitrobenzylthioinosine-sensitive nucleoside transporters (ENT1) in brain," *J Neurochem* 73(2):867-873, 1999.

Anderson et al., "Inhibition of human cytomegalovirus immediate-early gene expression by an antisense oligonucleotide complementary to immediate-early RNA," *Antimicrob Agents Chemother* 40(9):2004-11, 1996.

Arora et al., "Bioavailability and efficacy of Antisense morpholino oligomers targeted to c-myc and cytochrome P-450 3A2 following oral administration in rats," *Journal of Pharmaceutical Science* 91(4):1009-1018, 2002.

Astriab-Fisher et al., "Conjugates of antisense oligonucleotides with the Tat and antennapedia cell-penetrating peptides: effects on cellular uptake, binding to target sequences, and biologic actions," *Pharm. Res.* 19(6):744-754, 2002.

Bailey et al., "Cationic oligonucleotides can mediate specific inhibition of gene expression in Xenopus oocytes," *Nucleic Acids Res* 26(21):4860-4867, 1998.

Barawkar et al., "Synthesis, biophysical properties, and nuclease resistance properties of mixed backbone oligodeoxynucleotides containing cationic internucleoside guanidinium linkages: deoxynucleic guanidine|DNA chimeras", *Proc Natl Acad Sci USA*., 95(19):11047-11052, 1998.

Bielekova et al., "Encephalitogenic potential of the myelin basic protein peptide (amino acids 83-99), in multiple sclerosis: results of a phase II clinical trial with an altered peptide ligand," *Nature Medicine* 6(10):1167-1175, 2000.

Bielekova et al., "Expansion and functional relevance of high-avidity myelin-specific CD4+ T cells in multiple sclerosis," *The Journal of immunology* 172(6):3893-3904, 2004.

Bonham et al., "An assessment of the antisense properties of RNase H-competent and steric-blocking oligomers," *Nucleic Acids Res* 23(7):1197-1203, 1995.

Boudvillain et al., "Transplatin-modified oligo(2'-O-methyl ribonucleotide)s: a new tool for selective modulation of gene expression," *Biochemistry* 36(10):2925-2931, 1997.

Braasch et al., "Novel antisense and peptide nucleic acid strategies for controlling gene expression," *Biochemistry* 41:4503-4510, 2002.

Bracci et al., "Synthetic peptides in the form of dendrimers become resistance to protease activity," *The Journal of Biological Chemistry* 278(47):46590-46595, 2003.

Branch, "A good antisense molecule is hard to find," *TIBS* 23:45-49, 1998.

Brand, "Topical and transdermal delivery of antisense oligonucleotides," *Curr. Opin. Mol. Ther.* 3(3):244-248, 2001.

Braun et al., "Setting the stage for bench-to-bedside movement of anti-HIV RNA inhibitors-gene therapy for AIDS in macaques," *Frontier Biosciences* 11:838-851, 2006.

Burrows et al., "Regulation of encephalitogenic T cells with recombinant TCR ligands," *The Journal of Immunology* 164(12):6366-6371, 2000.

Burrows et al., "Two-domain MHC class II molecules form stable complexes with mylen basic protein 69-89 peptide that detect and inhibit rat encephalitogenic T cells and treat experimental autoimmune encephalomyelitis," *The Journal of Immunology* 161(11):5987-5996, 1998.

Chen et al., "A concise method for the preparation of peptide and arginine-rich peptide-conjugated antisense oligonucleotide," *Bioconjugate Chem.* 14:532-538, 2003.

Choudhury et al., "Inhibtion of HIV-1 replication by a Tat RNA-binding domain peptide analog," *Journal of Acquired Immune Deficiency Syndromes and Human Retrovirology* 17(2):104-111, 1998.

Chirila et al., "The use of synthetic polymers for delivery of therapeutic antisense oligodeoxynucleotides," *Biomaterials* 23(2):321-342, 2002.

Courcoul et al., "Peripheral blood mononuclear cells produce normal amounts of defective Vif—human immunodeficiency virus type 1 particles which are restricted for the preretrotranscription steps," *Journal of Virology*, 69(4):2068-2074, 1995.

Crooke, Antisense Drug Technology: Basic Principles of Antisense Technology. New York, Marcel Dekker, S. Crooke Ed Springer pp. 1-28, 2001.

Crooke, S. T., Antisense Drug Technology: Principles, Strategies, and Applications. New York, Marcel Dekker, S. Crooke Ed Springer pp. 108-118, 1999.

Daniel et al., "Protection of nonobese diabetic mice from diabetes by intranasal or subcutaneous administration of insulin peptide B-(9-23)," *Proc Natl Acad Sci USA* 93(2):956-960, 1996.

De Rosbo et al., "The myelin-associated oligodendrocytic basic protein region MOBP15-36 encompasses the immunodominant major encephalitogenic epitope(s) for SJL/J mice and predicted epitope(s) for multiple sclerosis-associated HLA-DRB1*1501," *The Journal of Immunology* 173(2):1426-1435, 2004.

Desrosiers et al., "Identification of highly attenuated mutants of simian immunodeficiency virus," *Journal of Virology*, 74(2):1431-1437, 1998.

Desrosiers, "HIV with multiple gene deletions as a live attenuated vaccine for AIDS," *AIDS Research and Human Retroviruses*, 8(3):411-421, 1992.

Dettenhofer et al., "Association of human immunodeficiency virus type 1 Vif with RNA and its role in reverse transcription," *Journal of Virology*, 74(19):8938-8945, 2000.

Ding et al., "An oligodeoxyribonucleotides N3'→ P5' phosphoramidate duplex forms an A-type helix in solution," *Nucleic Acids Res* 24(2):354-360, 1996.

Ellis et al., "Investigation of the putative immunodominant T cell epitopes in coeliac disease," *Gut* 52(2):212-217, 2003.

Falk et al., "induction and suppression of an autoimmune disease by oligomerized T cell epitopes: enhanced in vivio potency of encephalitogenic peptides," *J. Exp. Med.* 191(4):717-730, 2000.

Fanning et al., "Gene therapy for HIV/AIDS: the potential for a new therapeutic regimen," *The Journal of Gene Medicine*, 5:645-653, 2003.

(56) References Cited

OTHER PUBLICATIONS

Fraser et al., "Coeliac disease: in vivo toxicity of the putative immunodominant epitope," *Gut* 52(12):1698-1702, 2003.
Fujii et al., "The linkage of innate to adaptive immunity via maturing dendritic cells in vivo requires CD40 ligation in addition to antigen presentation and CD80/86 costimulation," *J. Exp. Med.* 199(12):1607-1618, 2004.
Gee et al., "Assessment of high-affinity hybridization, RNase H cleavage, and covalent linkage in translation arrest by antisense oligonucleotides," *Antisense Nucleic Acid Drug Dev.* 8(2):103-111, 1998.
Gewirtz et al., "Facilitating oligonucleotide delivery: helping antisense deliver on its promise", *Proc. Natl. Acad. Sci. U.S.A.*, 93,(8):3161-3163, 1996.
Gilbert et al., "Sieve analysis: methods for assessing from vaccine trial data how vaccine efficacy varies with genotypic and phenotypic pathogen variation," *Journal of Clinical Epidemiology*, 54:68-85, 2001.
Goncalves et al., "Role of Vif in human immunodeficiency virus type 1 reverse Transcription," *Journal of Virology*, 70(12):8701-8709, 1996.
Green et al., "Antisense oligonucleotides: an evolving technology for the modulation of gene expression in human disease", *Journal of American College of Surgeons*, 191.(1): 93-150, 2000.
Harris et al., "DNA deamination mediates innate immunity to retroviral infection," *Cell*, 113(6):803-809, 2003.
Hawiger et al., "Dendritic cells induce peripheral T cell unresponsiveness under steady state conditions in vivo," *J. Exp. Med.* 194(6):769-779, 2001.
Holz et al., "Myelin-associated oligodendrocytic basic protein: identification of an encephalitogenic epitope and association with multiple sclerosis," *The Journal of Immunology* 164:1103-1109, 2000.
Huan et al., "Monomeric recombinant TCR ligand reduced relapse rate and severity of experimental autoimmune encephalomyelitis in SJL/J mice though cytokine switch," *The Journal of Immunology* 172:4556-4566, 2004.
Huang et al., "A Polyethylene Glycol Copolymer for Carrying and Releasing Multiple Copies of Cysteine-Containing Peptides," *Bioconjugate Chemistry* 9(5):612-617, 1998.
Hudziak et al., "Antiproliferative effects of steric blocking phosphorodiamidate morpholino antisense agents directed against c-myc," *Antisense & Nucleic Acid Drug Development* 10(3):163-176, 2000.
Hudziak et al., "Resistance of morpholino phosphorodiamidate oligomers to enzymatic degradation," *Antisense Nucleic Acid Drug Dev.* 6(4):267-272, 1996.
International Search Report for International Application No. PCT/US2000/008174, mailed Jul. 25, 2000, 2 pages.
International Search Report for International Application No. PCT/US2008/088339, mailed Jun. 4, 2009, 4 pages.
International Search Report for International Application No. PCT/US2009/068599, mailed May 21, 2010, 5 pages.
Irmler et al., "Inhibition of death receptor signals by cellular FLIP," *Nature* 388(6638):190-195, 1997.
Isomura et al., "Antigen-Specific Peripheral Tolerance Induced by Topical Application of NF-κB Decoy Oligodeoxynucleotide," *Journal of Investigative Dermatology* 126:97-104, 2006.
Iversen et al., "Compositions for Enhancing Transport of Molecules Into Cells," U.S. Appl. No. 60/466,703, filed Apr. 29, 2003, 55 pages.
Jen et al., "Suppression of gene expression by targeted disruption of messenger RNA: available options and current strategies," *Stem Cells*, 18:307-319 (2000).
Jones et al., "Identification of autoantigens in psoriatic Plaques using expression cloning," *J. of Invest. Dermatol.* 123:93-100, 2004.
Kappos et al., "Induction of a non-encephalitogenic type 2 T helper-cell autoimmune response in multiple sclerosis after administration of an altered peptide ligand in a placebo-controlled, randomized phase II trial. The Altered Peptide Ligand in Relapsing MS Study Group," *Nature Medicine* 6(10):1176-1182, 2000.
Kinter et al., "HIV envelope induces virus expression from resting CD4+ T cells isolated from HIV-infected individuals in the absence of markers of cellular activation or apoptosis," *Journal of Immunology* 170(5):2449-2455, 2003.
Kirchhoff et al., "TCR-Mediated Up-Regulation of c-FLIPshort Correlates with Resistance Toward CD95-Mediated Apoptosis by Blocking Death-Induced Signaling Complex Activity," *J Immunol* 165:6293-6300, 2000.
Lazou et al., "The use of antisense strategy to modulate human melanogenesis," *J. Drugs Dermatol* 6(6Suppl):s2-7, 2007.
Lin et al., "Developmental and characterization of desmoglein-3 specific T cells from patients with pemphigus vulgaris," *J. Clin. Invest.* 99(1):31-40, 1997.
Linkletter et al., "Solid-phase synthesis of positively charged deoxynucleic guanidine (DNG) modified oligonucleotides containing neutral urea linkages: Effect of charge deletions on binding and fidelity," *Bioorg. Med. Chem.* 8(11):1893-1901, 2000.
Lisziewicz et al., "Specific inhibition of human immunodeficiency virus type 1 replication by antisense oligonucleotides: an in vitro model for treatment," *Proc. Natl. Acad. Sci.*, 89:1120.9-11213, 1992.
Liu et al., "Anti-peptide autoantibodies and fatal anaphylaxis in NOD mice in response to insulin self-peptides B:9-23 and B:13-23," *Journal of Clinical Investigation* 110(7):1021-1027, 2002.
Loke et al., "Characterization of oligonucleotide transport into living cells," *Proc Natl Acad Sci USA* 86(10):3474-3478, 1989.
Lu et al., "Antisense-mediated inhibition of human immunodeficiency virus (HIV) replication by use of an HIV type 1-based vector results in severely attenuated mutants incapable of developing resistance," *Journal of Virology*, 78(13):7079-7088, 2004.
Mantegazzi et al., "Anti-MOG autoantibodies in Italian multiple sclerosis patients: specificity, sensitivity and clinical association," *International Immunology* 16(3):559-565, 2004.
Mariani et al., "Species-specific exclusion of APOBEC3G from HIV-1 virions by Vif," *Cell*, 114.(1):21-31, 2003.
Marin et al., "HIV-1 Vif protein binds the editing enzyme APOBEC3G and induces its degradation," *Nature Medicine*, 9(11): 1398-1403, 2003.
Marshall et al., "Arginine-rich cell-penetration peptides facilitate delivery of antisense oligomers into murine leukocytes and alter pre-mRNA splicing," *Journal of Immunological Methods* 325:114-126, 2007.
Micheau, "Cellular FLICE-inhibitory protein: an attrav\ctive therapeutic target?," *Expert. Opin. Ther. Targets* 7:559-573, 2003.
Micklefield, "Backbone modification of nucleic acids: synthesis, structure and therapeutic applications," *Curr Med Chem.*, 8(10): 1157-79, 2001.
Moulton et al., "Cellular uptake of antisense morpholino oligomers conjugated to arginine-rich peptides," *Bioconjugate Chemistry* 15(2):290-299, 2004.
Moulton et al., "Compound and Method for Treating Myotonic Dystrophy," U.S. Appl. No. 12/493,140, filed Jun. 26, 2009, 80 pages.
Moulton et al., "HIV Tat Peptide Enhances Cellular Delivery of Antisense Morpholino Oligomers," *Antisense and Nucleic Acid Drug Development* 13:31-43, 2003.
Moulton et al., "Peptide-assisted delivery of steric-blocking antisense oligomers," *Curr Opin Mol Ther* 5(2):123-132, 2003.
Mourich et al., "Antisense Compound and Method for Selectively Killing Activated T Cells," U.S. Appl. No. 60/505,418, filed Sep. 23, 2003, 60 pages.
Mourich et al., "Antisense Targeting of cFLIP sensitizes Activated T Cells to Undergo Apoptosis and Desensitizes Responses to Contact Dermatitis," *Journal of Investigative Dermatology* 129:1945-1953, 2009.
Murphy et al., "Induction by antigen of intrathymic apoptosis of CD4+CD8+TCRlo thymocytes in vivo," *Science* 250(4988):1720-1723, 1990.
Nakayama et al., "Prime role for an insulin epitope in the development of type 1 diabetes in NOD mice," *Nature* 435(7039):220-223, 2005.
Nielsen et al., "Sequence-Selective Recognition of DNA by Strand Displacement with a Thymine-Substituted Polyamide," *Science Reports*, Dec. 6, 1991, pp. 1497-1500.

(56) References Cited

OTHER PUBLICATIONS

Opalinska et al., "Nucleic-acid therapeutics: basic principles and recent applications," *Nature Reviews/Drug Discovery* 1:503-514, 2002.
Palu et al., "In pursuit of new developments for gene therapy of human diseases," *Journal of Biotechnology* 68(1):1-13, 1999.
Pari et al., "Potent antiviral activity of an antisense oligonucleotide complementary to the intron-exon boundary of human cytomegalovirus genes UL36 and UL37," *Antimicrobial Agents Chemotherapy* 39(5):1157-1167, 1995.
Perlman et al., "FLICE-inhibitory Protein Expression during Macrophage Differentiation Confers Resistance to Fas-mediated Apoptosis," *The Journal of Experimental Medicine* 190(11):1679-1688, Dec. 6, 1999.
Rittner et al., "Identification and analysis of antisense RNA target regions of the human immunodeficiency virus type 1," *Nucleic Acids Research* 19(7):1421-1426, 1991.
Rothbard et al., "Arginine-rich molecular transporters for drug delivery: role of backbone spacing in cellular uptake," *J. Med. Chem.* 45:3612-3618, 2002.
Rotzschke et al., "Superactivation of an Immune response triggered by oligomerized T cell epitopes," *Proc Natl Acad Sci USA* 94:14642-14647, 1997.
Schmitz et al., "Resistance of Short Term Activated T Cells to CD95-Mediated Apoptosis Correlates with De Novo Protein Synthesis of c-FLIPshort," *J Immunol* 172:2194-2200, 2004.
Schubert et al., "Oligonucleotide-based antiviral strategies," *HEP* 173:261-287, 2006.
Shan et al., "Structural Basis for Gluten intolerance in Celiac Sprue," *Science* 297:2275-2279, 1997.
Sheehy et al., "Isolation of a human gene that inhibits HIV-1 infection and is suppressed by the viral Vif protein," *Nature* 418(6898):646-650, 2001.
Simon et al., "The human immunodeficiency virus type 1 Vif protein modulates the postpenetration stability of viral nucleoprotein complexes," *Journal of Virology* 70(8):5297-5305, 1996.
Stein et al., "A specificity comparison of four antisense types: morpholino, 2'-O-methyl RNA, DNA, and phosphorothioate DNA," *Antisense Nucleic Acid Drug Dev* 7(3):151-157, 1997.
Stein et al., Phosphorothioate Oligodeoxynucleotide Analogues, Boca Raton, FL, CRC Press, 1989, 21 pages.
Steinekemeier et al., "Vaccination, prevention, and treatment of experimental autoimmune neuritis (EAN) by an oligomerized T cell epitope," *Proc Natl Acad Sci USA* 98(24):13872-13877, 2001.
Summerton et al., "Morpholino and phosphorothioate antisense oligomers compared in cell-free and in-cell systems," *Antisense & Nucleic Acid Drug Development*, 7:63-70, 1997.
Summerton et al., "Morpholino antisense oligomers: design, preparation, and properties," *Antisense Nucleic Acid Drug Dev.* 7(3):187-195, 1997.
Summerton et al., "Morpholino antisense oligomers: the case for an RNase Hindependent structural type," *Biochim et. Biophys. ACTA*, 1489:141-158, 1999.
Suzuki et al., "Possible existence of common internalization mechanisms among arginine-rich peptides," *Journal of Biological Chemistry* 277(4):2437-2443, 2002.
Tamm et al., "Antisense therapy in oncology: new hope for an old idea?," *The Lancet* 358(9280):489-497, 2001.
Thorburn et al., "Death receptor-induced cell killing," *Cell Signal* 16:139-144, 2004.
Tondelli et al., "Native oligodeoxynucleotides specifically activate against human immunodeficiency virus type 1 in vitro: a G-quart-driven effect?," *Antimicrobial Agents and Chemotherapy* 40(9):2034-2038, 1996.
Torrebce et al., "Targeting RNA for degradation with a (2'-5')oligoadenylate-antisense chimera," *Proc Natl Acad Sci USA* 90:1300-1304, 1993.
Toulme et al., "Targeting RNA structres by antisense oligonucleotides," *Biochimie* 78(7):663-673, 1996.
Tung et al., "Dual-Specificity Interaction of HIV-1 TAR RNA with Tat Peptide-Oligonucleotide Conjugates," *Bioconjugate Chem.* 6:292-295, 1995.
Vandenbark et al., "Recombinant TCR ligand induces tolerance to myelin oligodendrocyte glycoprotein 35-55 peptide and reverses clinical and histological signs of chronic experimental autoimmune encephalomyelitis in HLA-DR2 transgenic mice," *The Journal of Immunology* 171(1):127-133, 2003.
Vanderlugt et al., "Pathologic role and temporal appearance of newly emerging autoepitopes in relapsing experimental autoimmune encephalomyelitis," *The Journal of Immunology* 164(2):670-678, 2000.
Vanin et al., "Synthesis and application of cleavable photactivable heterobifunctional reagents," *Biochemistry* 20:6754-6760, 1981.
Veldman et al., "Dichotomy of autoreactive Th1 and Th2 cell responses to desmoglein 3 in patients with pemphigus vulgaris (PV) and healthy carriers of PV-associated HLA class II alleles," *The Journal of immunology* 170(1):635-642, 2003.
Vives et al., "A truncated HIV-1 Tat protein basic domain rapidly translocates through the plasma membrane and accumulates in the cell nucleus," *Journal of Biological Chemistry* 272(25):16010-16017, 1997.
Wang et al., "Inhibition of Fas-mediated apoptosis by the B cell antigen receptor through c-FLIP," *Eur. J. Immunol.* 30:155-163, 2000.
Wasem et al., "Sensitizing antigen-specific CD8+ T cells for accelerated suicide causes immune incompetence," *J. Clin. Invest.* 111(8):1191-1199, 2003.
Wender et al., "The design, synthesis, and evaluation of molecules that enable or enhance cellular uptake: peptoid molecular transporters," *Proc Natl Acad Sci USA* 97(24):13003-13008, 2000.
Williams et al., "A single intra-articular injection of liposomally conjugated methotrexate suppresses joint inflammation in rat antigen-induced arthritis," *British Journal of Rheumatology* 35(8):719-724, 1996.
Wolkowicz et al., "Gene therapy progress and prospects: novel gene therapy approaches for AIDS," *Gene Therapy* 12(6):467-476, 2005.
Yakubov et al., "Mechanism of oligonucleotide uptake by cells: involvement of specific receptors?," *Proc Natl Acad Sci USA* 86(17):6454-6458, 1989.
You et al., "In vitro RNA synthesis from exogenous dengue viral RNA templates requires long range interactions between 5'- and 3'-terminal regions that influence RNA structure," *The Journal of Biological Chemistry* 276(19):15581-15591, 2001.
You et al., "Presence of diabetes-inhibiting, glutamic acid decarboxylase-specific, IL-10-dependent, regulatory T cells in Naïve nonobese diabetic mice," *The Journal of Immunology* 173(11):6777-6785, 2004.
Yu et al., "A predictable sequential determinant spreading cascade invariably accompanies progression of experimental autoimmune encephalomyelitis: a basis for peptide-specific therapy after onset of clinical disease," *J of Exp Med* 183(4):1777-1788, 1996.
Zhang et al., "inhibition of tumorigenicity of the teratoma PC cell line by transfection with antisense CDNA for PC cell-derived growth factor (PCDGF, epithelin/granulin precursor)," *Proc Natl Acad Sci USA* 95(24):14202-14207, 1998.
Zhu et al., "evidence for human immunodeficiency virus type 1 replication in vivo in CD14(+) monocytes and its potential role as a source of virus in patients on highly active antiviral therapy," *J. Virology* 76(2):707-716, 2002.
Zollinger et al., "Meningococcal vaccines—present and future," *Transactions of Royal Soc of Tropical Medicine and Hygiene* 85(Supp. 1):37-43, 1991.

* cited by examiner

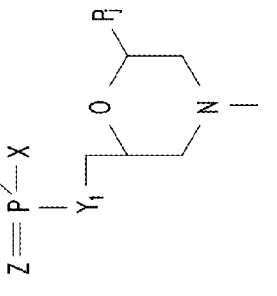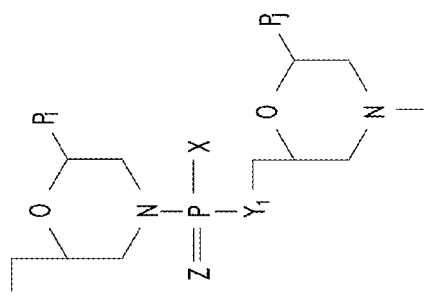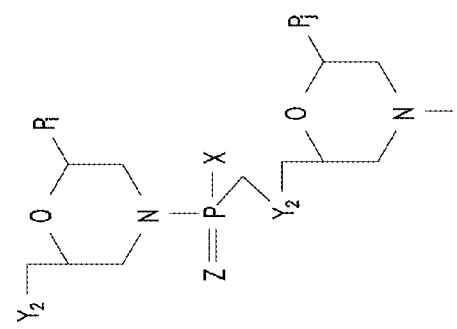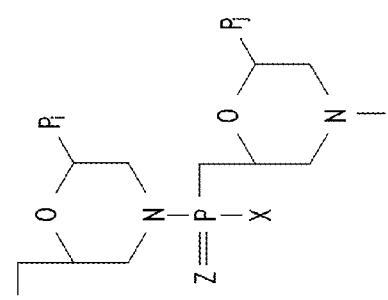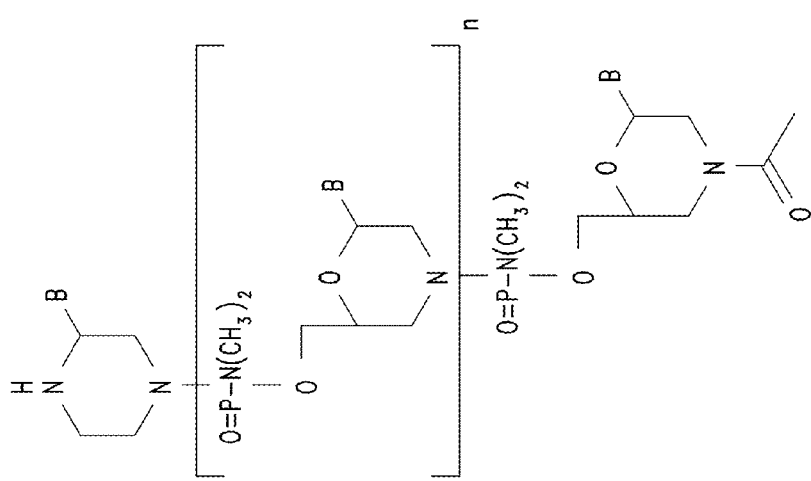
FIG. 1C
FIG. 1E
FIG. 1B
FIG. 1D
FIG. 1A Control

CFLAR PPMO
(SEQ ID NO. 28)

FITC

FITC + CFLAR PPMO
(SEQ ID NO. 28)

Reduction in Distribution of CFLAR Positive Cells Post FITC Challenge with Topical CFLAR PPMO
Control
FIG. 6A
CFLAR PPMO (SEQ ID NO. 28)
FIG. 6B
FITC
FIG. 6C
FITC + CFLAR PPMO (SEQ ID NO. 28)

ANTISENSE COMPOSITIONS AND METHODS FOR MODULATING CONTACT HYPERSENSITIVITY OR CONTACT DERMATITIS

CROSS-REFERENCE TO RELATED APPLICATION

This application claims the benefit under 35 U.S.C. §119 (e) of U.S. Provisional Patent Application No. 61/138,460 filed Dec. 17, 2008 which application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_409a_SEQUENCE_LISTING.txt. The text file is 10 KB, was created on Mar. 12, 2010, and is being submitted electronically via EFS-Web.

FIELD OF THE INVENTION

The present invention relates to methods and antisense compounds for modulating contact hypersensitivity responses induced by exposure to antigens, including haptens or metal ions complexed with cellular proteins.

REFERENCES

The following references are cited in the Background or Methods sections of this application.

Brand, R. M. (2001). "Topical and transdermal delivery of antisense oligonucleotides." Curr Opin Mol Ther 3(3): 244-8.
Brand, R. M. and P. L. Iversen (2000). "Transdermal delivery of antisense compounds." Adv Drug Deliv Rev 44(1): 51-7.
Isomura, I., K. Tsujimura, et al. (2006). "Antigen-specific peripheral tolerance induced by topical application of NF-kappaB decoy oligodeoxynucleotide." J Invest Dermatol 126(1): 97-104.
Kirchhoff, S., W. W. Muller, et al. (2000). "TCR-mediated up-regulation of c-FLIPshort correlates with resistance toward CD95-mediated apoptosis by blocking death-inducing signaling complex activity." J Immunol 165(11): 6293-300.
Lazou, K., N. S. Sadick, et al. (2007). "The use of antisense strategy to modulate human melanogenesis." J Drugs Dermatol 6(6 Suppl): s2-7.
Leung, D. Y., L. A. Diaz, et al. (1997). "Allergic and immunologic skin disorders." Jama 278(22): 1914-23.
Marshall, N. B., S. K. Oda, et al. (2007). "Arginine-rich cell-penetrating peptides facilitate delivery of antisense oligomers into murine leukocytes and alter pre-mRNA splicing." J Immunol Methods 325(1-2): 114-26.
Merk, H. F., J. M. Baron, et al. (2006). "Concepts in molecular dermatotoxicology." Exp Dermatol 15(9): 692-704.
Mourich, D. V., S. K. Oda, et al. (2007). "Ligand independent form of CTLA-4 induced by antisense EXON skipping in NOD mouse inhibits autoimmune diabetes." J Exp Med (In Press).
Perlman, H., L. J. Pagliari, et al. (1999). "FLICE-inhibitory protein expression during macrophage differentiation confers resistance to fas-mediated apoptosis." J Exp Med 190 (11): 1679-88.
Regnier, V., T. Le Doan, et al. (1998). "Parameters controlling topical delivery of oligonucleotides by electroporation." J Drug Target 5(4): 275-89.
Saint-Mezard, P., F. Berard, et al. (2004). "The role of CD4+ and CD8+ T cells in contact hypersensitivity and allergic contact dermatitis." Eur J Dermatol 14(3): 131-8.
Saint-Mezard, P., M. Krasteva, et al. (2003). "Afferent and efferent phases of allergic contact dermatitis (ACD) can be induced after a single skin contact with haptens: evidence using a mouse model of primary ACD." J Invest Dermatol 120(4): 641-7.
Saint-Mezard, P., A. Rosieres, et al. (2004). "Allergic contact dermatitis." Eur J Dermatol 14(5): 284-95.
Schmitz, I., H. Weyd, et al. (2004). "Resistance of short term activated T cells to CD95-mediated apoptosis correlates with de novo protein synthesis of c-FLIPshort." J Immunol 172(4): 2194-200.
Stein, C. A. and J. S. Cohen (1989). Phosphorothioate Oligodeoxynucleotide Analogues. Boca Raton, Fla., CRC Press.
Thorburn, A. (2004). "Death receptor-induced cell killing." Cell Signal 16(2): 139-44.
Wang, J., A. A. Lobito, et al. (2000). "Inhibition of Fas-mediated apoptosis by the B cell antigen receptor through c-FLIP." Eur J Immunol 30(1): 155-63.

BACKGROUND OF THE INVENTION

Contact dermatitis is responsible for over 5.6 million doctor visits each year in the United States and accounts for 15-20% of all occupational diseases. Including lost workdays and loss of productivity, the estimated total annual costs associated with occupational skin diseases approach $1 billion annually in the United States (CDC National Institute of Occupational Health, Update Jul. 1997) and up to $3 billion annually in Germany (Merk, Baron et al. 2006). Eighty percent of contact dermatitis instances are due to irritants while in the other 20% the compound induces an immunologic cascade and are classified as allergic (Leung, Diaz et al. 1997).

Contact dermatitis and many hypersensitivity reactions of the skin are produced by haptens, in the form of low molecular weight molecules or metal ions, complexing with cellular proteins. Subsequently these are processed into peptides and presented on the surface of antigen-presenting cells (APCs), typically Langerhans cells, the principle APC of the skin, residing in the epidermis (Saint-Mezard, Krasteva et al. 2003). Once Langerhans undergo maturation they migrate to the regional lymph node and present hapten-modified peptides in the context of major histocompatibility class I and II molecules to hapten-specific CD8+ and CD4+ T cells, respectively (Saint-Mezard, Berard et al. 2004). Antigen-specific activation of T cells constitutes the sensitization phase of contact sensitivity responses. Upon subsequent exposure to hapten, the challenge phase, effector memory T cells migrate to the peripheral tissues harboring hapten-presenting APCs. Here antigen recognition induces the T cells to express various mediators of inflammation and cytotoxicity, ultimately causing dermatitis and tissue damage (Saint-Mezard, Rosieres et al. 2004).

One of the anti-apoptotic proteins that is upregulated in T cells following T-cell activation is CFLAR (Kirchhoff, Muller et al. 2000). T cells that upregulate CFLAR as a consequence of T-cell receptor (TCR) engagement are resistant to Fas-mediated apoptosis. It has been clearly established that this CFLAR associated resistance correlates with de novo protein synthesis of $CFLAR_S$ (Schmitz, Weyd et al. 2004). In these studies, it was also shown that CFLAR exerted its anti-apoptotic effect by blocking DISC activity. Increased expression of CFLAR is also seen following cross-linking of the B-cell receptor for antigen. In this case the upregulation was seen in the levels of $CFLAR_L$ and was also associated with inhibition of Fas-mediated apoptosis (Wang, Lobito et al. 2000). CFLAR expression levels are also associated with the resistance to apoptosis that is seen following monocyte to macrophage differentiation (Perlman, Pagliari et al. 1999). It appears that CFLAR is commonly upregulated as a first step to prevent Fas-mediated apoptosis following signals for subsequent cell differentiation.

Although the signaling pathways associated with apoptosis and immunoregulation are complex and incompletely understood, CFLAR is one anti-apoptotic molecule that appears to play an important role in cell survival especially following death receptor ligation (Thorburn 2004).

A disclosure of antisense targeting of CFLAR, as shown in Mourich, et al (US20050203041 and WO2005030799), describes the use of such compounds to treat transplantation rejection and autoimmune conditions. The circulating T cells targeted by the methods and compositions of US20050203041 are activated by alloantigens that induce a graft versus host response in the case of transplantation and hyper-activated T cells responding to self antigens in the case of autoimmune conditions.

Accordingly, given the absence of a sufficient number of interventions for combating contact hypersensitivity, the present invention solves this deficiency while providing other related advantages.

SUMMARY OF THE INVENTION

The present invention is based in part on the discoveries that targeting CFLAR expression in cells circulating in the epidermal region of a subject is effective to produce tolerance to a sensitizing agent, including an agent known to provoke contact hypersensitivity such as contact dermatitis; and that such targeting can be achieved by topical delivery to the subject of an antisense oligonucleotide such as a morpholino oligonucleotide. In certain embodiments, the oligonucleotide may be conjugated to cell-penetrating peptide, such as an arginine-rich peptide, and delivered in a suitable topical delivery vehicle.

The invention includes, in one aspect, a method of inducing tolerance to a sensitizing agent known to provoke contact hypersensitivity in a subject. The method includes topically applying to the subject, an effective amount of an antisense composition containing, in a suitable topical delivery vehicle, an antisense oligonucleotide containing between 12-40 nucleotide bases and having a base sequence effective to hybridize to at least 12 contiguous bases of a target sequence contained within SEQ ID NO:11, wherein the oligonucleotide binding to the target sequence is effective to block normal expression of a functional human CFLAR in CFLAR-expressing lymphocytes.

In certain embodiments, the antisense oligonucleotide is composed of morpholino subunits and phosphorus-containing intersubunit linkages joining a morpholino nitrogen of one subunit to a 5' exocyclic carbon of an adjacent subunit. In certain embodiments, the oligonucleotide comprises an cell-penetrating peptide such as an arginine-rich peptide that enhances uptake of the oligonucleotide into activated T cells in culture.

The method may further include continuing the applying step on a periodic basis as long as needed to reduce skin or mucous membrane inflammation resulting from contact with the agent.

Where the sensitizing agent to which the subject is exposed is a skin irritant, such as an acid, an alkali such as a soap or detergent, a solvent, a heavy metal, rubber, a cosmetic, or a fragrance, the composition in certain embodiments may be applied to the skin area of the subject expected to come into contact with the irritant.

Where the sensitizing agent to which the subject is exposed is a skin allergen, such as poison oak, poison ivy, poison sumac, or other plants containing urushiol oil, the composition in certain embodiments may be applied to the skin area of the subject expected to come into contact with the allergen.

In certain embodiments, the delivery vehicle in the composition may include propylene glycol and an acyl-chain lipid, such as a fatty acid or phospholipids. One exemplary acyl-chain lipid is linoleic acid.

In certain embodiments, the oligonucleotide in the conjugate may have a base sequence effective to hybridize to at least 12 contiguous bases of a target sequence contained within SEQ ID NO:12. The arginine-rich peptide in the conjugate may have a sequence identified by any one of SEQ ID NO:1-10.

In certain embodiments, the morpholino subunits in the compound may be joined by phosphorodiamidate linkages, in accordance with the structure:

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino e.g., wherein $X=NR_2$, where each R is independently hydrogen or methyl. The intersubunit linkages, which are uncharged, may be interspersed with linkages that are positively charged at physiological pH, where the total number of positively charged linkages is between 2 and no more than half of the total number of linkages. An exemplary positively charged linkage is the above phosphorodiamidate structure in which X is 1-piperazine.

Certain embodiments include compositions for use in treating contact hypersensitivity in a subject, by topical application of the composition to an effected skin area of the subject. In certain embodiments, the composition includes an antisense oligonucleotide containing between 12-40 nucleotide bases and having a base sequence effective to hybridize to at least 6 contiguous bases of a target sequence contained within SEQ ID NO:11, where oligonucleotide binding to the target sequence is effective to block normal expression of a functional human CFLAR in CFLAR-expressing lymphocytes exposed to the oligonucleotide.

In certain embodiments, the antisense oligonucleotide is composed of morpholino subunits and phosphorus-containing intersubunit linkages joining a morpholino nitrogen of one subunit to a 5' exocyclic carbon of an adjacent subunit. In certain embodiments, the oligonucleotide is a conjugate that comprises an arginine-rich peptide capable of enhancing uptake of the oligonucleotide into activated T cells in culture.

In still another aspect, the invention includes a method of achieving transdermal uptake of an antisense oligonucleotide into target cells in the epidermis, by applying to the skin or mucous membrane of a subject, an antisense composition comprising an antisense oligonucleotide that is conjugated to a cell-penetrating peptide as described herein. Exemplary embodiments of the method are as noted above.

Certain embodiments include methods of treating contact hypersensitivity, comprising contacting the skin or mucous membrane of a subject with an effective amount of an antisense composition containing an antisense oligonucleotide as described herein, wherein the oligonucleotide reduces expression of a functional human CFLAR in CFLAR-expressing lymphocytes. In certain embodiments, the oligonucleotide is a peptide nucleic acid (PNA), a locked nucleic acid (LNA), an RNA interference agent with a duplex region, or a morpholino oligomer.

These and other objects and features of the invention will become more fully apparent when the following detailed description of the invention is read in conjunction with the accompanying drawings.

BRIEF DESCRIPTION OF THE DRAWINGS

FIGS. 1A-1E show exemplary backbone linkages in a morpholino oligomer;

DETAILED DESCRIPTION OF THE INVENTION

I. Definitions

Figure 2A:
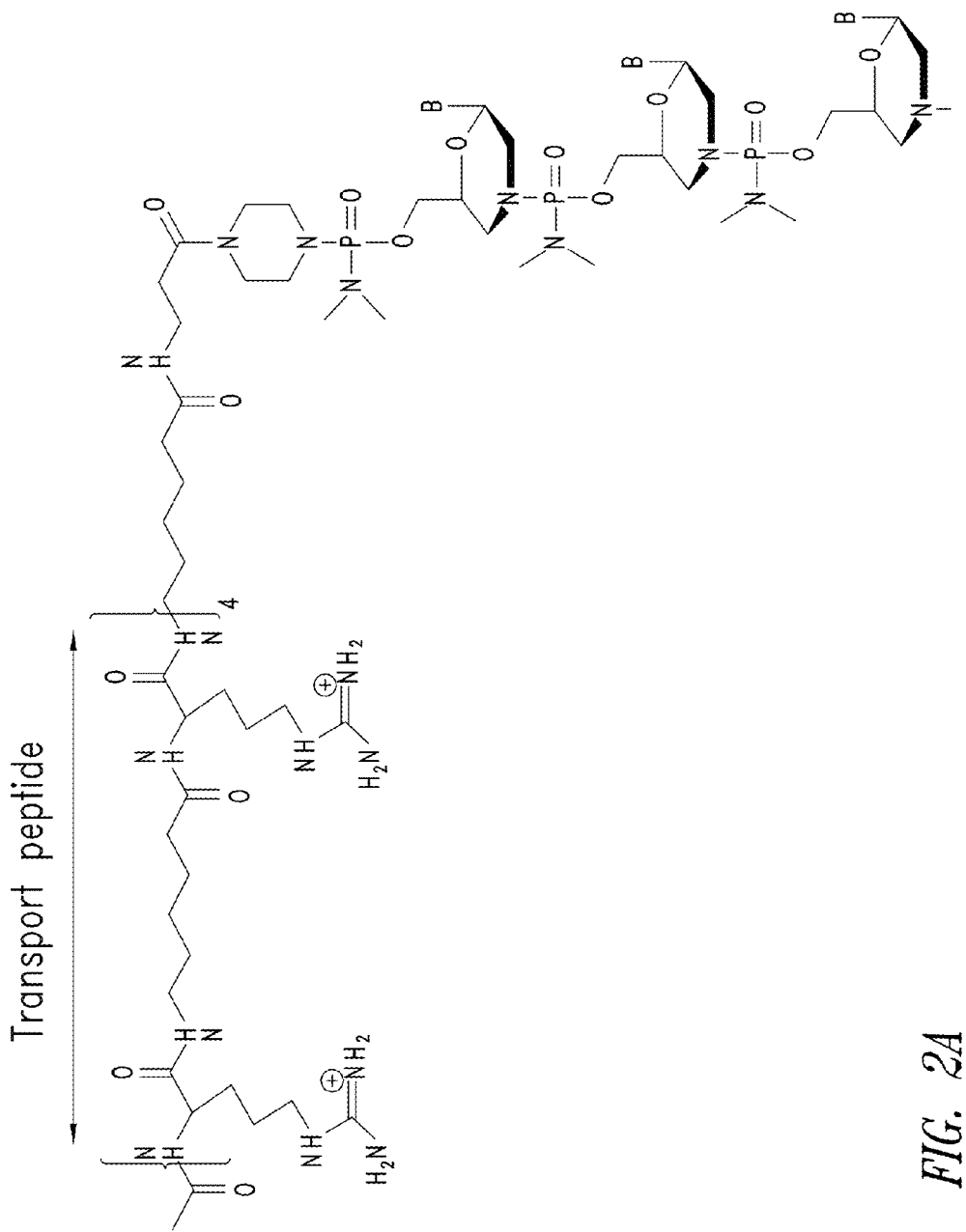
FIGS. 2A and 2B show a conjugate of an arginine-rich peptide and an uncharged PMO oligomer (2A), and a conjugate of an arginine-rich peptide and a PMO have uncharged linkages and two different types of positively charged linkages (2B)

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Polynucleotides are described as "complementary" to one another when hybridization occurs in an antiparallel configuration between two single-stranded polynucleotides. Complementarity (the degree that one polynucleotide is complementary with another) is quantifiable in terms of the proportion of bases in opposing strands that are expected to form hydrogen bonds with each other, according to generally accepted base-pairing rules.

Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5' and/or 3' terminus.

The terms "cell penetrating peptide" or "CPP" are used interchangeably and refer to cationic cell penetrating peptides, also called transport peptides, carrier peptides, or peptide transduction domains. The peptides, as illustrated, have the capability of inducing cell penetration within 30%, 40%, 50%, 60%, 70%, 80%, 90%, or 100% of cells of a given cell culture population, including all integers in between, and allow macromolecular translocation within multiple tissues in vivo upon systemic administration. A cell-penetrating peptide may enhance uptake of the oligonucleotide into T-cells, including activated T-cells, quiescent T-cells, or both. A peptide may be an arginine-rich peptide, including the peptides in SEQ ID NOS:1-10.

The terms "antisense oligomer" or "antisense oligonucleotide" or "antisense compound" are used interchangeably and refer to a sequence of subunits, each having a base carried on a backbone subunit composed of ribose or other pentose sugar or morpholino group, and where the backbone groups are linked by intersubunit linkages that allow the bases in the compound to hybridize to a "target sequence" in a nucleic acid (typically an RNA) by Watson-Crick base pairing, to form a nucleic acid:oligomer heteroduplex within the target sequence. The cyclic subunits may be based on ribose or another pentose sugar or, in certain embodiments, a morpholino group (see description of morpholino oligomers below). Included are single-stranded antisense oligomers, and antisense oligomers having at least one duplex or double-stranded region. Also included are peptide nucleic acids (PNAs), locked nucleic acids (LNAs), RNA interference agents (e.g., siRNA agents), and other antisense agents known in the art.

The oligomer may have exact sequence complementarity to the target sequence or near complementarity. Such antisense compounds are designed to block or inhibit translation of the mRNA containing the target sequence or designed to block pre-mRNA processing (i.e., splicing) and may be said to be "directed to" a sequence with which it hybridizes. Antisense oligonucleotides and oligonucleotide analogs may contain between about 8 and 40 subunits, typically about 8-25 subunits, and preferably about 12 to 25 subunits.

Antisense oligomers can be designed to block or inhibit translation of mRNA or to inhibit natural pre-mRNA splice processing, or induce degradation of targeted mRNAs, and may be said to be "directed to" or "targeted against" a target sequence with which it hybridizes. In certain embodiments, the target sequence includes a region including an AUG start codon of a CFLAR mRNA, a 3' or 5' splice site of a pre-processed CFLAR mRNA, or a branch point of a pre-processed CFLAR mRNA. The target sequence may be within an exon or within an intron. The target sequence for a splice site may include an mRNA sequence having its 5' end 1 to about 25 base pairs downstream of a normal splice acceptor junction in a preprocessed mRNA. A preferred target sequence for a splice is any region of a preprocessed mRNA that includes a splice site or is contained entirely within an exon coding sequence or spans a splice acceptor or donor site.

Included are antisense oligonucleotides that comprise, consist essentially of, or consist of one or more of SEQ ID NOS:23-33. Also included are variants of these antisense oligomers, including variant oligomers having 80%, 85%, 90%, 95%, 97%, 98%, or 99% (including all integers in between) sequence identity or sequence homology to any one of SEQ ID NOS: 23-33, and/or variants that differ from these sequences by about 1, 2, 3, 4, 5, 6, 7, 8, 9, or 10 nucleotides, preferably those variants that reduce CFLAR expression in a cell such as a T-cell. Also included are oligonucleotides of any one or more of SEQ ID NOS: 23-33, which comprise a suitable number of charged linkages, as described herein, e.g., up to about 1 per every 2-5 uncharged linkages, such as about 4-5 per every 10 uncharged linkages, and/or which comprise an Arg-rich peptide attached thereto, as also described herein.

A "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligomer is composed of morpholino subunit structures linked together by phosphoramidate or phosphorodiamidate linkages, joining the morpholino nitrogen of one subunit to the 5' exocyclic carbon of an adjacent subunit, each subunit including a purine or pyrimidine base-pairing moiety effective to bind, by base-specific hydrogen bonding, to a base in a polynucleotide. Morpholino oligomers (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

A "phosphoramidate" group comprises phosphorus having three attached oxygen atoms and one attached nitrogen atom, while a "phosphorodiamidate" group (see e.g. FIGS. 1A-B) comprises phosphorus having two attached oxygen atoms and two attached nitrogen atoms. In the uncharged or the cationic intersubunit linkages of the oligomers described herein, one nitrogen is always pendant to the backbone chain. The second nitrogen in a phosphorodiamidate linkage is typically the ring nitrogen in a morpholino ring structure (again, see FIGS. 1A-B). A phosphoramidate or phosphorodiamidate linkage may include a thiophosphoramidate or thiophosphorodiamidate linkage, respectively, in which one oxygen atom, typically the oxygen pendant to the backbone in the oligomers described herein, is replaced with sulfur.

The terms "uncharged" and "cationic" are used herein to refer to the predominant charge state of a backbone linking groups in an antisense compound at near-neutral pH, e.g. about 6 to 8. Preferably, the term refers to the predominant state of the chemical moiety at physiological pH, that is, about 7.4. A "substantially uncharged," phosphorus containing backbone in an oligonucleotide analog is one in which a majority of the subunit linkages, e.g., between 50-100%, typically at least 60% to 100% or 75% or 80% of its linkages, are uncharged at physiological pH, and contain a single phosphorous atom.

A "subunit" of an oligonucleotide refers to one nucleotide (or nucleotide analog) unit. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage).

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5''-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U (see, e.g., Sequence Listing).

An "amino acid subunit" or "amino acid residue" can refer to an α-amino acid residue (—CO—CHR—NH—) or a β- or other amino acid residue (e.g., —CO—(CH$_2$)$_n$CHR—NH—), where R is a side chain (which may include hydrogen) and n is 1 to 6, preferably 1 to 4.

The term "naturally occurring amino acid" refers to an amino acid present in proteins found in nature, such as the 20 (L)-amino acids utilized during protein biosynthesis as well as others such as 4-hydroxyproline, hydroxylysine, desmosine, isodesmosine, homocysteine, citrulline and ornithine. The term "non-natural amino acids" refers to those amino acids not present in proteins found in nature, examples include beta-alanine (n-Ala), 6-aminohexanoic acid (Ahx) and 6-aminopentanoic acid. Additional examples of "non-natural amino acids" include, without limitation, (D)-amino acids, norleucine, norvaline, p-fluorophenylalanine, ethionine and the like, which are known to a person skilled in the art.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that has been removed from the sequences that are normally adjacent to the fragment.

A first sequence is an "antisense sequence" with respect to a second sequence if a polynucleotide whose sequence is the first sequence specifically binds to, or specifically hybridizes with, the second polynucleotide sequence under physiological conditions.

The term "target sequence" refers to a portion of the target RNA against which the oligonucleotide or antisense agent is directed, that is, the sequence to which the oligonucleotide will hybridize by Watson-Crick base pairing of a complementary sequence.

The term "targeting sequence" is the sequence in the oligonucleotide analog that is complementary (meaning, in addition, substantially complementary) to the "target sequence" in either the mature CFLAR mRNA or a pre-processed mRNA transcript, and specifically the pre-processed mRNA transcript of the human CFLAR gene. The entire targeting sequence, or only a portion, of the compound may be complementary to the target sequence. For example, in an antisense compound having about 10-40 bases, about 6, 7, 8, 9, 10, 11, 12, 13, 14, 15, 16, 17, 18, 19, or 20, 21, 22, 23, 24, 25, 26, 27, 28, 29, 30, 31, 32, 33, 34, 35, 36, 37, 38, 39, or 40 may be targeting sequences. Typically, the targeting sequence is formed of contiguous bases in the compound, but may alternatively be formed of non-contiguous sequences that when placed together, e.g., from opposite ends of the compound, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary." Preferably, the oligonucleotide analog compounds employed in the presently described methods have at most one mismatch with the target sequence out of 10 nucleotides, and preferably at most one mismatch out of 20. Alternatively, the antisense compounds employed have at least 90% sequence homology, and preferably at least 95% sequence homology, with the exemplary targeting sequences as designated herein. For purposes of complementary binding to an RNA target, and as discussed below, a guanine base may be complementary to either an adenine or uracil RNA base.

An oligonucleotide "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense compound to the target sequence, as well as with exact complementarity.

"Homology" refers to the percentage number of amino acids that are identical or constitute conservative substitutions. Homology may be determined using sequence comparison programs such as GAP (Deveraux et al., 1984, *Nucleic Acids Research* 12, 387-395). In this way sequences of a similar or substantially different length to those cited herein could be compared by insertion of gaps into the alignment, such gaps being determined, for example, by the comparison algorithm used by GAP.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence," "comparison window," "sequence identity," "percentage of sequence identity," and "substantial identity". A "reference sequence" is at least 8 or 10 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window"

refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonucleotide analog and the complementary portion of a target RNA. A "nuclease-resistant heteroduplex" refers to a heteroduplex formed by the binding of an antisense compound to its complementary target, such that the heteroduplex is substantially resistant to in vivo degradation by intracellular and extracellular nucleases, such as RNAse H, which are capable of cutting double-stranded RNA/RNA or RNA/DNA complexes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Monocytes, lymphocytes, and dendritic cells" refer to three types of white blood cells of the immune system. The cell types have their common, textbook definitions.

The term "activated T cells" refers to either chronically activated T cells (i.e. autoimmunity) or naive T cells responding to alloantigens (i.e. transplantation), or chemical modification of self-antigens, (hapten-induced contact sensitivity).

The acronym "CFLAR" refers to the CASP8 and FADD-like apoptosis regulator and also has several other designations including: FLICE inhibitory protein; FADD-like anti-apoptotic molecule; Inhibitor of FLICE; Caspase-related inducer of apoptosis; Caspase homolog; Caspase-like apoptosis regulatory protein; and usurpin beta. CFLAR also refers to the protein with the following aliases: CASH; CASP8AP1; CLARP; Casper; FLAME; FLAME-1; FLAME1; FLIP; I-FLICE; MRIT; USURPIN; cFLIP, c-FLIPL; c-FLIPR; and c-FLIPS. The human CFLAR NCBI Gene ID is 8837 and the GenBank reference sequence for the human CFLAR gene can be found using accession NM_003879.

The acronym "PMO" refers to a phosphorodiamidate morpholino oligonucleotide.

An arginine-rich peptide refers to a peptide transport moiety effective to enhance transport of the compound into cells. The transport moiety may be attached to a terminus of the oligomer and in certain embodiments consists of about 6 to 16 amino acid subunits selected from subunits with a guanidyl side chain moiety, as in the alpha amino acid subunit arginine (Arg) and the beta amino acid subunits defined by —CO—$(CH_2)_n$—CHR—NH—, where n is 2 to 7 and R is H. For example, when n is 5 and R is H, the subunit is a 6-aminohexanoic acid subunit; when n is 2 and R is H, the subunit is a β-alanine subunit.

The acronym "PPMO" refers to a peptide-conjugate of an arginine-rich peptide and a PMO.

An agent is "effective to enhance transport" or "effective to promote uptake" of the compound into mammalian cells if the compound is taken up by these cells by passive transport across the cell membrane or by an active transport mechanism involving, for example, transport across the membrane by e.g., an ATP-dependent transport mechanism, or by "facilitated transport", referring to transport of antisense agents across the cell membrane by a transport mechanism that requires binding of the agent to a transport protein, which then facilitates passage of the bound agent across the membrane, or by cell membrane invagination. Uptake of the compound into the target cells may be confirmed, for example, by uptake of a fluoresceinated compound in the cells.

An "effective amount" or "therapeutically effective amount" refers to an amount of antisense compound administered topically to a mammalian subject, either as a single dose or as part of a series of doses, which is effective to produce a desired therapeutic effect, such as reduced inflammation, reduction in dermatitis, reduced localized infiltration of lymphocytes, or any combination thereof. For an antisense oligomer, this effect is typically brought about by inhibiting translation or natural splice-processing of a selected target sequence, such as CFLAR.

By "enhance" or "enhancing," or "increase" or "increasing," or "stimulate" or "stimulating," refers generally to the ability of one or antisense or RNAi compounds or compositions to produce or cause a greater physiological response (i.e., downstream effects) in a cell or a subject, as compared to the response caused by either no antisense compound or a control compound. Examples of a physiological response included increased activation-induced cell death (AICD) of T-cells, including CD4+ and CD8+ T-cells. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7, 1.8, etc.) the amount produced by no antisense compound (the absence of an agent) or a control compound.

The term "reduce" or "inhibit" may relate generally to the ability of one or more antisense or RNAi compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in CFLAR expression, T-cell activation or infiltration, inflammation, or the various symptoms of contact hypersensitivity. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

A "topical delivery vehicle" or carrier refers generally to a pharmaceutical composition appropriate for application to the skin or mucous membranes. Certain illustrative delivery vehicles incorporate propylene glycol and/or an acyl-chain lipid, e.g., fatty acid, fatty ester, phospholipid, and triglycerides. An exemplary acyl-chain lipid is linoleic acid. Other exemplary topical formulations are described below.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically, simultaneously or subsequent to the initiation of a pathologic event or contact with an etiologic agent. Treatment includes any desirable effect on the symptoms or pathology of a disease or condition associated contact hypersensitivity. The related term "improved therapeutic outcome" relative to a patient diagnosed as having such a condition, may refer to a slowing or diminution in the condition, or detectable symptoms associated with the condition.

Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

A "subject," as used herein, may include any animal that exhibits a symptom, or is at risk for exhibiting a symptom, which can be treated with an antisense compound of the invention, such as a subject that has or is at risk for having contact hypersensitivity, or related symptoms. Suitable subjects (patients) include laboratory animals (such as mouse, rat, rabbit, or guinea pig), farm animals, and domestic animals or pets (such as a cat or dog). Non-human primates and, preferably, human patients, are included.

A subject is "sensitized" to an etiologic agent if the extent of contact dermatitis, e.g., inflammatory response to the agent, is more severe than response from the initial contact with the agent. The degree of sensitization may increase with subsequent exposure(s) to the agent, and may decline during a prolonged period without exposure to the agent.

"Inducing tolerance" to a sensitizing agent known to provoke contact hypersensitivity including contact dermatitis means reducing the extent to which a sensitized subject reacts to skin contact with the agent, as evidenced, for example, by a reduced inflammatory response at the skin or mucous membrane site of contact with the agent.

"Alkyl" refers to a fully saturated monovalent radical containing carbon and hydrogen, which may be branched, linear, or cyclic (cycloalkyl). Examples of alkyl groups are methyl, ethyl, n-butyl, t-butyl, n-heptyl, isopropyl, cyclopropyl, cyclopentyl, ethylcyclopentyl, and cyclohexyl. Generally preferred are alkyl groups having one to six carbon atoms, referred to as "lower alkyl", and exemplified by methyl, ethyl, n-butyl, i-butyl, t-butyl, isoamyl, n-pentyl, and isopentyl. In one embodiment, lower alkyl refers to $C_i$ to $O_4$ alkyl.

"Alkenyl" refers to an unsaturated monovalent radical containing carbon and hydrogen, which may be branched, linear, or cyclic. The alkenyl group may be monounsaturated or polyunsaturated. Generally preferred are alkenyl groups having one to six carbon atoms, referred to as "lower alkenyl."

"Alkynyl" refers to an unsaturated straight or branched chain hydrocarbon radical containing from 2 to 18 carbons comprising at least one carbon to carbon triple bond. Examples include without limitation ethynyl, propynyl, isopropynyl, butynyl, iso-butynyl, tert-butynyl, pentynyl and hexynyl. The term "lower alkynyl" refers to an alkynyl group, as defined herein, containing between 2 and 8 carbons.

"Cycloalkyl" refers to a mono- or poly-cyclic alkyl radical. Examples include without limitation cyclobutyl, cyclopentyl, cyclohexyl, cycloheptyl and cyclooctyl.

"Aryl" refers to a substituted or unsubstituted monovalent aromatic radical, generally having a single ring (e.g., phenyl) or two condensed rings (e.g., naphthyl). This term includes heteroaryl groups, which are aromatic ring groups having one or more nitrogen, oxygen, or sulfur atoms in the ring, such as furyl, pyrrolyl, pyridyl, and indolyl. By "substituted" is meant that one or more ring hydrogens in the aryl group is replaced with a halide such as fluorine, chlorine, or bromine; with a lower alkyl group containing one or two carbon atoms; nitro, amino, methylamino, dimethylamino, methoxy, halomethoxy, halomethyl, or haloethyl. Preferred substituents include halogen, methyl, ethyl, and methoxy. Generally preferred are aryl groups having a single ring.

"Aralkyl" refers to an alkyl, preferably lower ($C_1$-$C_4$, more preferably $C_1$-$C_2$) alkyl, substituent which is further substituted with an aryl group; examples are benzyl (—$CH_2C_6H_5$) and phenethyl (—$CH_2CH_2C_6H_5$).

"Thioalkoxy" refers to a radical of the formula —SRc where Rc is an alkyl radical as defined herein. The term "lower thioalkoxy" refers to an alkoxy group, as defined herein, containing between 1 and 8 carbons.

"Alkoxy" refers to a radical of the formula —ORda where Rd is an alkyl radical as defined herein. The term "lower alkoxy" refers to an alkoxy group, as defined herein, containing between 1 and 8 carbons. Examples of alkoxy groups include, without limitation, methoxy and ethoxy.

"Alkoxyalkyl" refers to an alkyl group substituted with an alkoxy group.

"Carbonyl" refers to the —C(=O)— radical.

"Guanidynyl" refers to the $H_2N(C=NH_2)$—NH— radical.

"Amidinyl" refers to the $H_2N(C=NH_2)CH$— radical.

"Amino" refers to the —$NH_2$ radical.

"Alkylamino" refers to a radical of the formula —NHRd or —NRdRd where each Rd is, independently, an alkyl radical as defined herein. The term "lower alkylamino" refers to an alkylamino group, as defined herein, containing between 1 and 8 carbons.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Preferably, the ring atoms include 3 to 6 carbon atoms. Such heterocycles include, for example, pyrrolidine, piperidine, piperazine, and morpholine.

Heterocycles include heteroaryls as defined below. Thus, in addition to the heteroaryls listed below, heterocycles also include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydrothiophenyl, tetrahydrothiopyranyl, tetrahydropyrimidinyl, tetrahydrothiopyranyl, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

The term "substituted", with respect to an alkyl, alkenyl, alkynyl, aryl, aralkyl, or alkaryl group, refers to replacement of a hydrogen atom with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

In certain embodiments, the terms "optionally substituted alkyl", "optionally substituted alkenyl", "optionally substituted alkoxy", "optionally substituted thioalkoxy", "optionally substituted alkyl amino", "optionally substituted lower alkyl", "optionally substituted lower alkenyl", "optionally substituted lower alkoxy", "optionally substituted lower thioalkoxy", "optionally substituted lower alkyl amino" and "optionally substituted heterocyclyl" mean that, when substituted, at least one hydrogen atom is replaced with a substituent. In the case of an oxo substituent (=O) two hydrogen atoms are replaced. In this regard, substituents include: deuterium, optionally substituted alkyl, optionally substituted alkenyl, optionally substituted alkynyl, optionally substituted aryl, optionally substituted heterocycle, optionally substituted cycloalkyl, oxo, halogen, —CN, —ORx, NRxRy, NRxC(=O)Ry, NRxSO2Ry, —NRxC(=O)NRxRy, C(=O)Rx, C(=O)ORx, C(=O)NRxRy, —SOmRx and —SOmNRxRy, wherein m is 0, 1 or 2, Rx and Ry are the same or different and independently hydrogen, optionally substituted alkyl, optionally substituted alkenyl, optionally substituted alkynyl, optionally substituted aryl, optionally substituted heterocycle or optionally substituted cycloalkyl and each of said optionally substituted alkyl, optionally substituted alkenyl, optionally substituted alkynyl, optionally substituted aryl, optionally substituted heterocycle and optionally substituted cycloalkyl substituents may be further substituted with one or more of oxo, halogen, —CN, —ORx, NRxRy, NRxC(=O)Ry, NRxSO2Ry, —NRxC(=O) NRxRy, C(=O)Rx, C(=O)ORx, C(=O)NRxRy, —SOmRx and —SOmNRxRy.

Target and Targeting Sequences

In certain embodiments, the antisense compound of the invention targets the AUG start site codon of a CFLAR mRNA. In certain embodiments, the oligonucleotide has a base sequence effective to hybridize to at least 6, 7, 8, 9, 10, 11, 12, 13, 14, 15, 17, 18, 19, 20, 21, 22, 23, 24, 25, 26, 27, 28, 29, 30, 31, 32, 33, 34, 35, 36, 37, 39, 39, 40 or more contiguous or non-contiguous bases of surrounding or spanning the AUG start codon of a human CFLAR mRNA transcript, such as the region within SEQ ID NO:11, and block or reduce normal expression of a functional human CFLAR in CFLAR expressing lymphocytes. Certain exemplary targeting sequences are able to hybridize to at least 12 contiguous bases contained within SEQ ID NO:12, and include SEQ ID NOS: 23-27, and variants thereof having at least about 80%, 85%, 90%, 95%, or 98% identity to these sequences.

In certain embodiments, the antisense compound of the invention may target a human CFLAR splice-site target sequence, such as a splice acceptor site, a splice donor site, or a branch point. Included are splice acceptor and splice donor sites at or near the border of any one of exons 1, 2, 3, 4, 5, 6, 7, 8, 9, 10, 11, 12, 13, or 14 of the various alternatively spliced mRNAs that derive from the CFLAR gene. Specific examples included splice acceptor and splice donor sites at or near the border of any one of exons 1, 3, 4, 5, 6, 8, 9, 10, 12, or 13 of C-FLIP$_L$, exons 3, 4, 5, 6, or 7 of C-FLIP$_S$, and exons 3, 4, 5, 6, or 7 of C-FLIP$_R$. Also included are branch points, which are typically located about 20-50 bases upstream of an acceptor site. Hence, in certain embodiments, an antisense oligomer may target about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more bases surrounding a splice donor or splice acceptor site or branch point of a CFLAR mRNA transcript.

In certain embodiments, an antisense compound may target a splice site contained within SEQ ID NOS:13-17. Human CFLAR splice-site target sequences contained within SEQ ID NOS:13-17 include any contiguous sequence of bases, typically at least 6 to 12 to 22 to 25 to 30 or more contiguous or non-contiguous bases (including all integers in between), at which hybridization by an antisense oligonucleotide is effective to block or reduce normal processing of a functional human CFLAR in CFLAR expressing lymphocytes. Exemplary targeting sequences include SEQ ID NOS:29-33, and variants thereof having at least about 80%, 85%, 90%, 95%, or 98% identity to these sequences.

Exemplary human (Hu) and murine (Mu) CFLAR target sequences are shown below in Table 1.

TABLE 1

Exemplary CFLAR Target Sequences

| Target | Target Sequence (5' to 3') | SEQ ID NO: |
|---|---|---|
| Hu-AUG (+)) | CCTTGTGAGCTTCCCTAGTCTAAGAGTAGGATGT CTGCTGAAGTCATCCATCAGGTTGAA | 11 |
| Hu-AUG (+12) | TCTAAGAGTAGGATGTCTGCTGAAG | 12 |
| Hu-Ex2SA | CAGAAAAATTCCCTTTTAACCACAG/AACT CCCCCACTGGAAAGGATTCTG | 13 |
| Hu-Ex3SA | CTAAATGAACTTGTCTGGTTTGCAG/ AGTGCTGATGGCAGAGATTGGTGAG | 14 |
| Hu-Ex4SA | TGTTTTTTGTTGGTGGTTCTCTTAG/ AGTTTCTTGGACCTTGTGGTTGAGT | 15 |
| Hu-Ex2SD | ACCCTCACCTTGTTTCGGACTATAG/ GTAATTCATCAACTCTTCCTGAGGC | 16 |
| Hu-Ex3SD | CCGAGGCAAGATAAGCAAGGAGAAG/ GTGAGTTTTCTTCTTTTGGTTCATG | 17 |
| Mu-Ex2SA | ATAAGAGGATTCTCTTTCACCACAG/ AGTGTCTCTATTGCAAGAACTCTGA | 18 |
| Mu-Ex2SD | ACCCTCACCTGGTTTCTGATTATAG/ GTAAGTCATCCCCTGGGGAGGGGA | 19 |
| Mu-Ex3SA | CTGAAGACACTTTTATGGTTTACAG/ GGTCCTGCTGATGGAGATTGGTGAG | 20 |

TABLE 1-continued

Exemplary CFLAR Target Sequences

| Target | Target Sequence (5' to 3') | SEQ ID NO: |
|---|---|---|
| Mu-Ex3SD | CAGAGGCAAGATAGCCAAGGACAAG/ GTGAGTTGTCTTTGCTCGGTGCCTG | 21 |
| Mu-Ex4SA | CATTTCTTGTTCATGGCTTTCTTAG/ AGTTTCTTGGATCTGGTGATTGAAT | 22 |

Human (hu) and murine (mu) CFLAR antisense targeting sequences that are complementary to regions contained within the target sequences listed in Table 1 are shown below in Table 2.

TABLE 2

Exemplary Human and Mouse CFLAR Targeting Sequences

| Oligomer | Sequence (5' to 3') | SEQ ID NO: |
|---|---|---|
| CFLAR-huAUG1 | CTTCAGCAGACATCCTACTC | 23 |
| CFLAR-huAUG2 | GACTAGGGAAGCTCACAAGG | 24 |
| CFLAR-huAUG3 | TCAACCTGATGGATGACTTC | 25 |
| CFLAR-huAUG(-5) | GATGACTTCAGCAGACATCCTAC | 26 |
| CFLAR-huAUG(-11) | CTTCAGCAGACATCCTACTCTTAG | 27 |
| CFLAR-muAUG | CTGGGCCATGTTCAGAACC | 28 |
| CFLAR-huSA2 | GGAGTTCTGTGGTTAAAAGG | 29 |
| CFLAR-huSD2 | CTATAGTCCGAAACAAGGTGAGG | 30 |
| CFLAR-huSA3 | CACCAATCTCTGCCATCAGCACT | 31 |
| CFLAR-huSA4 | TCAACCACAAGGTCCAAGAAACT | 32 |
| CFLAR-huSD3 | CTTCTCCTTGCTTATCTTGCCT | 33 |
| $R_9F_2$-CFLARmuAUG; CFLAR PPMO | RRRRRRRRRFFC-CTGGGCCATGTTCAGAACC | 34 |
| Scrambled Control | TGCGCGTCATGTACGCCAA | 35 |
| $R_9F_2$-Scr. Control; Scrambled Control PPMO | RRRRRRRRRFFC-TGCGCGTCATGTACGCCAA | 36 |

Additional targeting sequences may be selected by first identifying an AUG translation start site or splice-site target sequence within SEQ ID NOS: 11-16, and constructing a targeting sequence complementary to at least 12 contiguous bases, and typically 20 or more bases, of the target sequence.

Once a targeting sequence has been identified, it can be readily tested for its ability to interfere with normal CFLAR expression or processing, through steps described below. Briefly, in one illustrative embodiment, a morpholino antisense compound (PMO) or peptide-conjugated morpholino antisense compound (PPMO) be prepared according to methods described in Sections B and C below, and the compound can be tested for its ability to block normal CFLAR expression or processing in CFLAR producing cells in accordance with the methods given in Example 1. This process can be applied to other antisense and RNAi chemistries and methodologies.

More generally, any type of assay or determination used to measure levels of CFLAR isoforms in culture samples may be employed, such as, but not limited to, immunoassays, including direct competitive, sandwich, direct and indirect cellular, and crisscross enzyme-linked immunosorbent assays (ELISAs), enzyme linked immunosorbent spot (ELISPOT) assays, radioimmunoassays (RIAs), immunoprecipitation, immunohistochemistry, immunofluorescence, immunoblotting, and the like may be employed using polyclonal, monoclonal, polyclonal, and fusion phage antibodies. Simple immunofluorescence using monoclonal and/or fusion phage antibodies are especially preferred in many embodiments. Moreover, the sequence of CFLAR is known so that assessment of mRNA levels by RT-PCR, ribonuclease protection assays, or Northern analysis, are feasible and in many cases preferred.

In certain embodiments, the antisense compound can be tested for its ability to block normal expression or processing of CFLAR by direct screening of the compound in a test animal, e.g., murine model, where the sequence tested is targeted against a selected AUG translation start site or splice site target sequence of the corresponding animal (mice) CFLAR processed or preprocessed transcript sequence. In this approach, the test agent is administered to the experimental animal, a biological sample is taken from the animal and from a control animal of the same species, and the CFLAR protein or mRNA concentration of the spliced products are measured.

Antisense Oligonucleotides

As detailed above, the antisense oligonucleotides described herein typically comprise a base sequence targeting a region that includes one or more of the following: the region surrounding the AUG start codon of a CFLAR mRNA, a region surrounding the splice donor or acceptor sites of a CFLAR mRNA, or a region surrounding the branch points of a CFLAR mRNA. In addition, the oligomer is able to effectively reduce expression of CFLAR mRNA in a cell, such as an activated T-cell. This requirement is typically met when the oligomer compound (a) has the ability to be actively taken up by mammalian cells, and (b) once taken up, form a duplex with the target RNA with a Tm greater than about 45° C.

A variety of antisense chemistries may be employed. Examples include RNA interference based compounds (e.g., siRNA, shRNA, or RNAi-inducing vectors), hybrid interfering RNA molecules, RNA amidates and thioamidates, thio-siRNA aptamers, phosphorothioates, shRNA without interferon and/or cytotoxicity induction (e.g., having one or a plurality of G(s) at the 5' end of the sense strand), DNA and antisense RNA hybrid constructs, oligomers having universal bases that can pair with all of the four naturally occurring bases, alternate oligonucleotide analogue chemistries in U.S. Application No. 2009/0149404 (herein incorporated by reference), 2' and/or 3' prodrugs of 1', 2', 3' or 4'-branched nucleosides, immunostimulatory oligonucleotide analogs (see, e.g., U.S. Application Nos. 2008/0027214 and 2006/0135454, herein incorporated by reference), ssDNA, bicyclonucleoside oligonucleotide analogues, circularly permuted chimeric pRNA molecules, caged RNAs (e.g., photoactivatable caged RNAs), self-cleaving ribozymes, oligonucleotides with alternating segments of sugar-modified nucleosides and 2'-deoxynucleosides, polyamide nucleic acid derivatives, oligos comprising a 5'- and/or a 3'-cap structure, chimeric nucleic acid molecules (e.g., having a target region and a largely double-stranded region of specific nucleotide sequences for intracellular targeting, siDNA, and oligomers of ribose groups linked by achiral 5' to 3' internucleoside phosphate linkages.

In certain embodiments, the oligomer backbone may be substantially uncharged, and, preferably, may be recognized as a substrate for active or facilitated transport across the cell membrane. The ability of the oligomer to form a stable duplex with the target RNA may also relate to other features of the oligomer backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm.

Certain embodiments included peptide nucleic acids (PNAs), analogs of DNA in which the backbone is structurally homomorphous with a deoxyribose backbone, consisting of N-(2-aminoethyl)glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

Certain embodiments employ morpholino-based subunits bearing base-pairing moieties, joined by uncharged linkages, as described above. Especially preferred is a substantially uncharged phosphorodiamidate-linked morpholino oligomer. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, and in PCT application No. US08/088339, all of which are expressly incorporated by reference herein.

Certain properties of the morpholino-based subunits include: the ability to be linked in a oligomeric form by stable, uncharged backbone linkages; the ability to support a nucleotide base (e.g., adenine, cytosine, guanine or uracil) such that the polymer formed can hybridize with a complementary-base target nucleic acid, including target RNA, with high Tm, even with oligomers as short as 10-14 bases; the ability of the oligomer to be actively transported into mammalian cells; and the ability of the oligomer:RNA heteroduplex to resist RNase degradation.

Figure 2B:
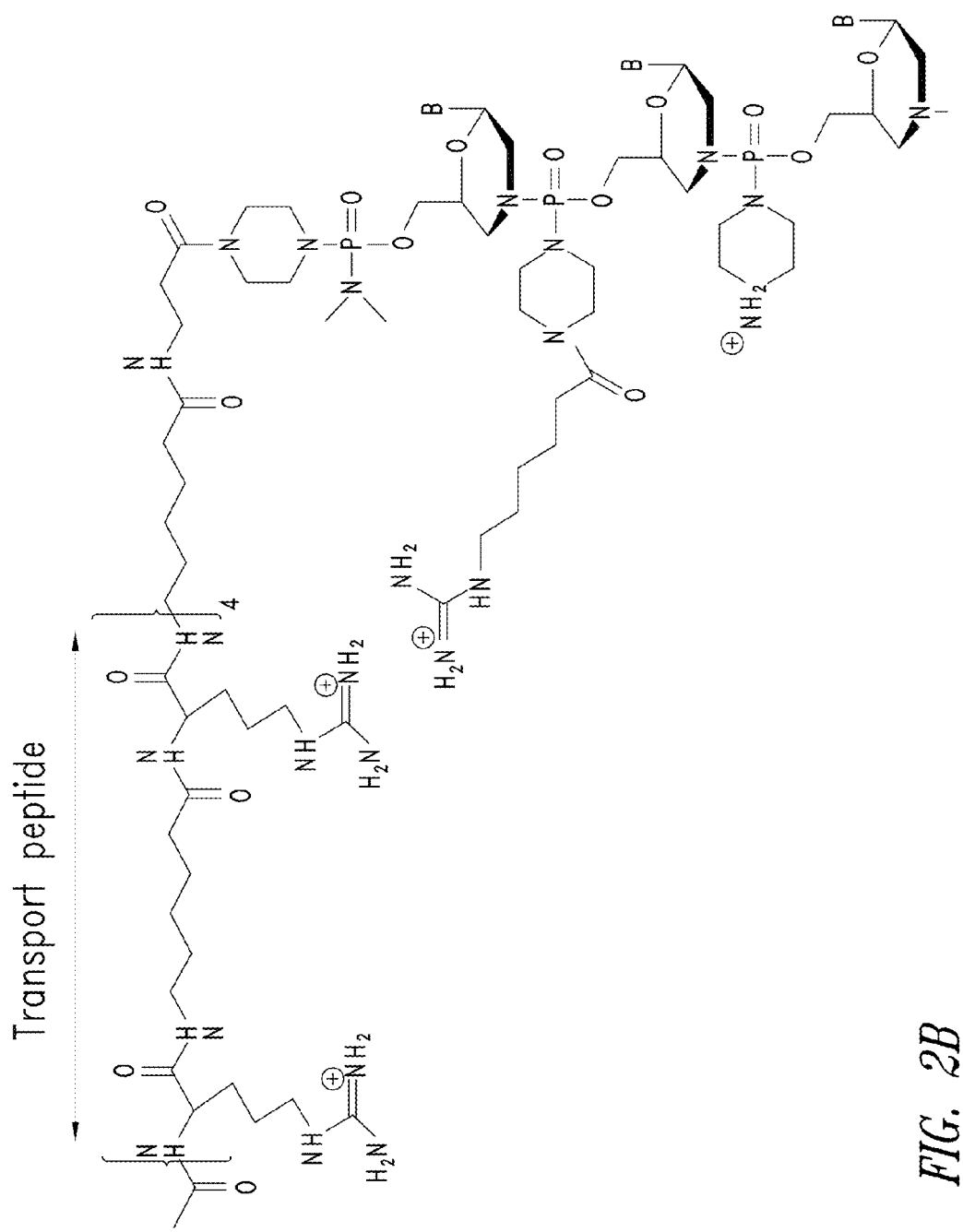

Examples of morpholino oligomers having phosphorus-containing backbone linkages are illustrated in FIGS. 1A, 2A-B. Especially preferred is a phosphorodiamidate-linked morpholino oligonucleotide such as shown in FIG. 2B, which is modified, in accordance with one aspect of the present invention, to contain positively charged groups at preferably about 10%-50% of its backbone linkages. Morpholino oligonucleotides with uncharged backbone linkages, including antisense oligonucleotides, are detailed, for example, in (Summerton and Weller 1997) and in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Properties of the morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil and inosine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into mammalian cells; and 4) the ability of the antisense oligonucleotide:RNA heteroduplex to resist RNAse and RNaseH degradation, respectively.

Exemplary backbone structures for antisense oligonucleotides of the claimed subject matter include the morpholino subunit types shown in FIGS. 1B-E, each linked by an uncharged or positively charged, phosphorus-containing subunit linkage. FIG. 1B shows a phosphorus-containing linkage which forms the five atom repeating-unit backbone, where the morpholino rings are linked by a 1-atom phosphoamide linkage. FIG. 1C shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

The linkages shown in FIGS. 1D and 1E are designed for 7-atom unit-length backbones. In structure 1D, the X moiety is as in Structure 1C, and the Y moiety may be methylene, sulfur, or, preferably, oxygen. In Structure 1E, the X and Y moieties are as in Structure 1C. Particularly preferred morpholino oligonucleotides include those composed of morpholino subunit structures of the form shown in FIG. 1C, where $X=NH_2$, $N(CH_3)_2$, or 1-piperazine or other charged group, $Y=O$, and $Z=O$.

As noted above, the substantially uncharged oligonucleotide may be modified, in accordance with an aspect of the invention, to include charged linkages, e.g. up to about 1 per every 2-5 uncharged linkages, such as about 4-5 per every 10 uncharged linkages. Optimal improvement in antisense activity may be seen when about 25% of the backbone linkages are cationic. In certain embodiments, enhancement may be seen with a small number e.g., 10-20% cationic linkages, or where the number of cationic linkages are in the range 50-80%, such as about 60%.

Additional experiments conducted in support of the present invention indicate that the enhancement seen with added cationic backbone charges may, in some cases, be further enhanced by distributing the bulk of the charges close of the "center-region" backbone linkages of the antisense oligonucleotide, e.g., in a 20mer oligonucleotide with 8 cationic backbone linkages, having at least 70% of these charged linkages localized in the 10 centermost linkages.

In certain embodiments, the antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, the antisense compound can be constructed to contain a selected number of cationic linkages interspersed with uncharged linkages of the type described above. The intersubunit linkages, both uncharged and cationic, preferably are phosphorus-containing linkages, having the structure:

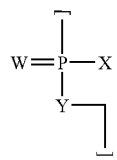

where
W is S or O, and is preferably O,
$X=NR^1R^2$ or $OR^6$,
$Y=O$ or $NR^7$,
and each said linkage in the oligomer is selected from:
(a) uncharged linkage (a), where each of $R^1$, $R^2$, $R^6$ and $R^7$ is independently selected from hydrogen and lower alkyl;
(b1) cationic linkage (b1), where $X=NR^1R^2$ and $Y=O$, and $NR^1R^2$ represents an optionally substituted piperazino group, such that $R^1R^2=$—CHRCHRN($R^3$)($R^4$)CHRCHR—, where
each R is independently H or $CH_3$,
$R^4$ is H, $CH_3$, or an electron pair, and
$R^3$ is selected from H, lower alkyl, e.g. $CH_3$, C(=NH)$NH_2$, Z-L-NHC(=NH)$NH_2$, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;
(b2) cationic linkage (b2), where $X=NR^1R^2$ and $Y=O$, $R^1=H$ or $CH_3$, and $R^2=LNR^3R^4R^5$, where L, $R^3$, and $R^4$ are as defined above, and $R^5$ is H, lower alkyl, or lower (alkoxy)alkyl; and
(b3) cationic linkage (b3), where $Y=NR^7$ and $X=OR^6$, and $R^7=LNR^3R^4R^5$, where L, $R^3$, $R^4$ and $R^5$ are as defined above, and $R^6$ is H or lower alkyl;
and at least one said linkage is selected from cationic linkages (b1), (b2), and (b3).

In certain embodiments, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 60%, and preferably 20-50% linkages may be cationic linkages.

In one embodiment, at least one linkage is of type (b1), where, preferably, each R is H, $R^4$ is H, $CH_3$, or an electron pair, and $R^3$ is selected from H, lower alkyl, e.g. $CH_3$, C(=NH)$NH_2$, and C(O)-L-NHC(=NH)$NH_2$. The latter two embodiments of $R^3$ provide a guanidino moiety, either attached directly to the piperazine ring, or pendant to a linker group L, respectively. For ease of synthesis, the variable Z in $R^3$ is preferably C(O) (carbonyl), as shown.

The linker group L, as noted above, contains bonds in its backbone selected from alkyl (e.g. —$CH_2$—$CH_2$—), alkoxy (—C—O—), and alkylamino (e.g. —$CH_2$—NH—), with the proviso that the terminal atoms in L (e.g., those adjacent to carbonyl or nitrogen) are carbon atoms. Although branched linkages (e.g. —$CH_2$—$CHCH_3$—) are possible, the linker is preferably unbranched. In one embodiment, the linker is a hydrocarbon linker. Such a linker may have the structure —$(CH_2)_n$—, where n is 1-12, preferably 2-8, and more preferably 2-6.

The morpholino subunits have the structure:

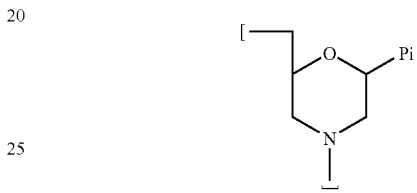

(i) where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

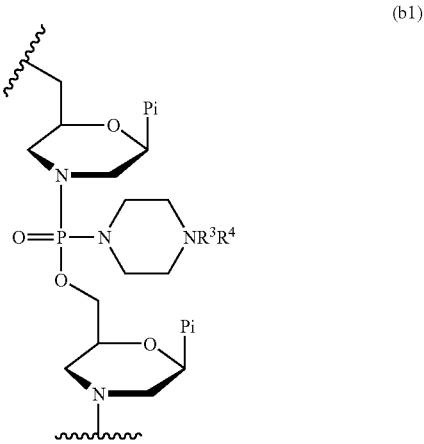

-continued

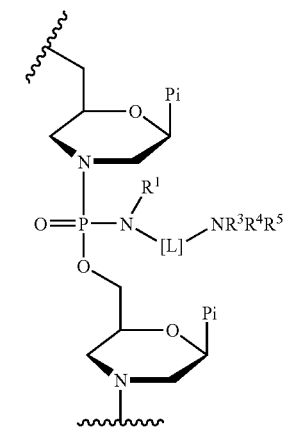
(b2)

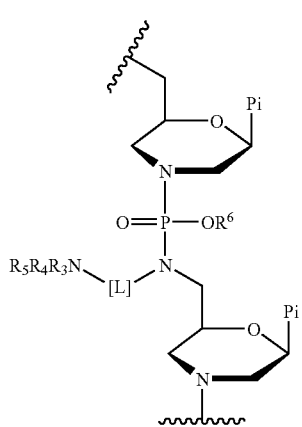
(b3)

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1') is referred to herein as a "Pip" linkage and (b1") is referred to herein as a "GuX" linkage:

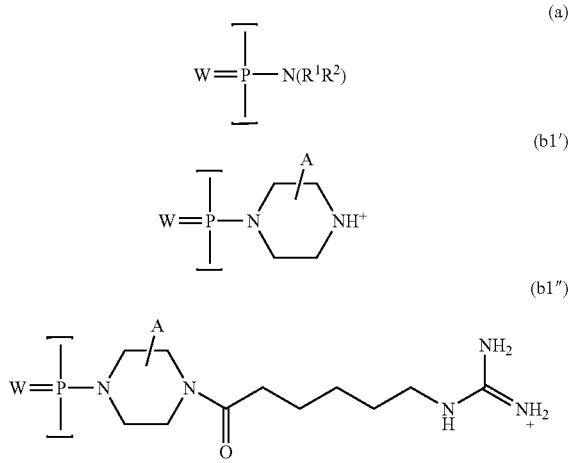

In the structures above, W is S or O; each of $R^1$ and $R^2$ is independently selected from hydrogen and lower alkyl, and is preferably methyl; and A represents hydrogen or a non-interfering substituent on one or more carbon atoms in (b1') and (b1"). In certain embodiments, the ring carbons in the piperazine ring are unsubstituted; however, they may include non-interfering substituents, such as methyl or fluorine. In certain embodiments, at most one or two carbon atoms is so substituted.

In further embodiments, at least 10% of the linkages are of type (b1') or (b1"); for example, 10%-60% and preferably 20% to 50%, of the linkages may be of type (b1') or (b1"). In certain embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5' nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g. four to eight, cationic linkages, and the remainder uncharged linkages. An oligomer having 14-15 subunits may ideally have two to seven, e.g., 3, 4, or 5, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine.

RNA Interference Agents

The CFLAR target regions described herein may also be targeted by a variety of RNA interference-based methods. RNA interference (RNAi) is an evolutionarily conserved gene-silencing mechanism, originally discovered in studies of the nematode *Caenorhabditis elegans* (Lee et al, Cell 75:843, 1993; Reinhart et al., Nature 403:901, 2000). It may be triggered by introducing dsRNA into cells expressing the appropriate molecular machinery, which then degrades the corresponding endogenous mRNA. The mechanism involves conversion of dsRNA into short RNAs that direct ribonucleases to homologous mRNA targets (summarized, Ruvkun, Science 2294:797, 2001).

In certain embodiments, the methods provided herein may utilize double-stranded ribonucleic acid (dsRNA) molecules as modulating agents, for reducing CFLAR expression, and thereby reducing hypersensitivity or contact dermatitis. dsRNAs generally comprise two single strands. One strand of the dsRNA comprises a nucleotide sequence that is substantially identical to a portion of the target gene or target region (the "sense" strand), and the other strand (the "complementary" or "antisense" strand) comprises a sequence that is substantially complementary to a portion of the target region. The strands are sufficiently complementary to hybridize to form a duplex structure. In certain embodiments, the complementary RNA strand may be less than 30 nucleotides, less than 25 nucleotides in length, or even 19 to 24 nucleotides in length. In certain aspects, the complementary nucleotide sequence may be 20-23 nucleotides in length, or 22 nucleotides in length.

In certain embodiments, at least one of the RNA strands comprises a nucleotide overhang of 1 to 4 nucleotides in length. In other embodiments, the dsRNA may further comprise at least one chemically modified nucleotide. In certain aspects, a dsRNA comprising a single-stranded overhang of 1 to 4 nucleotides may comprise a molecule wherein the unpaired nucleotide of the single-stranded overhang that is directly adjacent to the terminal nucleotide pair contains a purine base. In other aspects, the last complementary nucleotide pairs on both ends of a dsRNA are a G-C pair, or, at least two of the last four terminal nucleotide pairs are G-C pairs.

Certain embodiments of the present invention may comprise microRNAs. Micro-RNAs represent a large group of small RNAs produced naturally in organisms, some of which regulate the expression of target genes. Micro-RNAs are formed from an approximately 70 nucleotide single-stranded hairpin precursor transcript by Dicer. (V. Ambros et al. Current Biology 13:807, 2003). Micro-RNAs are not translated into proteins, but instead bind to specific messenger RNAs, thereby blocking translation. It is thought that micro-RNAs base-pair imprecisely with their targets to inhibit translation. Certain micro-RNAs may be transcribed as hairpin RNA precursors, which are then processed to their mature forms by Dicer enzyme.

In certain embodiments, the modulating agent, or RNAi oligonucleotide, is single stranded. In other embodiments, the modulating agent, or RNAi oligonucleotide, is double stranded. Certain embodiments may also employ short-interfering RNAs (siRNA). In certain embodiments, the first strand of the double-stranded oligonucleotide contains two more nucleoside residues than the second strand. In other embodiments, the first strand and the second strand have the same number of nucleosides; however, the first and second strands are offset such that the two terminal nucleosides on the first and second strands are not paired with a residue on the complimentary strand. In certain instances, the two nucleosides that are not paired are thymidine resides.

In instances when the modulating agent comprises siRNA, the agent should include a region of sufficient homology to the target region, and be of sufficient length in terms of nucleotides, such that the siRNA agent, or a fragment thereof, can mediate down regulation of the target RNA. It will be understood that the term "ribonucleotide" or "nucleotide" can, in the case of a modified RNA or nucleotide surrogate, also refer to a modified nucleotide, or surrogate replacement moiety at one or more positions. Thus, an siRNA agent is or includes a region which is at least partially complementary to the target RNA. It is not necessary that there be perfect complementarity between the siRNA agent and the target, but the correspondence must be sufficient to enable the siRNA agent, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments include one or more but preferably 10, 8, 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the over all double-strand character of the molecule.

In addition, an siRNA modulating agent may be modified or include nucleoside surrogates. Single stranded regions of an siRNA agent may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA agent, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

siRNA agents may include, for example, molecules that are long enough to trigger the interferon response (which can be cleaved by Dicer (Bernstein et al. 2001. Nature, 409:363-366) and enter a RISC(RNAi-induced silencing complex)), in addition to molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter RNAi agents herein. "siRNA agent or shorter RNAi agent" as used refers to an siRNA agent that is sufficiently short that it does not induce a deleterious interferon response in a human cell, e.g., it has a duplexed region of less than 60 but preferably less than 50, 40, or 30 nucleotide pairs. An siRNA modulating agent, or a cleavage product thereof, can down regulate a target gene, e.g., by inducing RNAi with respect to a target RNA, preferably a CFLAR mRNA.

Each strand of an siRNA modulating agent can be equal to or less than 35, 30, 25, 24, 23, 22, 21, or 20 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides.

In addition to homology to target RNA and the ability to down regulate a target gene, an siRNA modulating agent may have one or more of the following properties: it may, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA; it may, despite modifications, even to a very large number, or all of the nucleosides, still have "RNA-like" properties, i.e., it may possess the overall structural, chemical and physical properties of an RNA molecule, even though not exclusively, or even partly, of ribonucleotide-based content. For example, an siRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a C.sub.3'-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into H-bonding which is more characteristic of the OH moiety of a ribonucleotide than the H moiety of a deoxyribonucleotide.

A "single strand RNAi agent" as used herein, is an RNAi agent which is made up of a single molecule. It may include a duplexed region, formed by intra-strand pairing, e.g., it may be, or include, a hairpin or pan-handle structure. Single strand RNAi modulating agents are preferably antisense with regard to the target molecule. A single strand RNAi agent should be sufficiently long that it can enter the RISC and participate in RISC mediated cleavage of a target mRNA. A single strand RNAi agent is at least 14, and more preferably at least 15, 20, 25, 29, 35, 40, or 50 nucleotides in length. It is preferably less than 200, 100, or 60 nucleotides in length.

Hairpin RNAi modulating agents may have a duplex region equal to or at least 17, 18, 19, 29, 21, 22, 23, 24, or 25 nucleotide pairs. The duplex region may preferably be equal to or less than 200, 100, or 50, in length. Certain ranges for the duplex region are 15-30, 17 to 23, 19 to 23, and 19 to 21 nucleotides pairs in length. The hairpin may have a single strand overhang or terminal unpaired region, preferably the 3', and preferably of the antisense side of the hairpin. In certain embodiments, overhangs are 2-3 nucleotides in length.

Certain modulating agents utilized according to the methods provided herein may comprise RNAi oligonucleotides such as chimeric oligonucleotides, or "chimeras," which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. Consequently, comparable results can often be obtained with shorter oligonucleotides when chimeric oligonucleotides are used, compared to phosphorothioate oligodeoxynucleotides. Chimeric oligonucleotides may be formed as composite structures of two or more oligonucleotides, modified oligonucleotides, oligonucleotides and/or oligonucleotide mimetics as described above. Such oligonucleotides have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; and 5,955,589, each of which is herein incorporated by reference. In certain embodiments, the chimeric oligonucleotide is RNA-DNA, DNA-RNA, RNA-DNA-RNA, DNA-RNA-DNA, or RNA-DNA-RNA-DNA, wherein the oligonucleotide is between 5 and 60 nucleotides in length.

In one aspect of the invention, modulating agents, such as RNAi agents, relate to an oligonucleotide comprising at least one ligand tethered to an altered or non-natural nucleobase. A large number of compounds can function as the altered base. The structure of the altered base is important to the extent that the altered base should not substantially prevent binding of the oligonucleotide to its target, e.g., mRNA. In certain embodiments, the altered base is difluorotolyl, nitropyrrolyl, nitroimidazolyl, nitroindolyl, napthalenyl, anthrancenyl, pyridinyl, quinolinyl, pyrenyl, or the divalent radical of any one of the non-natural nucleobases described herein. In certain embodiments, the non-natural nucleobase is difluorotolyl, nitropyrrolyl, or nitroimidazolyl. In certain embodiments, the non-natural nucleobase is difluorotolyl. A wide variety of ligands are known in the art and are amenable to the present invention. For example, the ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, the ligand is a steroid or aromatic compound. In certain instances, the ligand is cholesteryl.

In other embodiments, the RNAi agent is an oligonucleotide tethered to a ligand for the purposes of improving cellular targeting and uptake. For example, an RNAi agent may be tethered to an antibody, or antigen binding fragment thereof. As an additional example, an RNAi agent may be tethered to a specific ligand binding molecule, such as a polypeptide or polypeptide fragment that specifically binds a particular cell-surface receptor.

In other embodiments, the modulating agent comprises a non-natural nucleobase. In certain embodiments, the non-natural nucleobase is difluorotolyl, nitroimidazolyl, nitroindolyl, or nitropyrrolyl. In certain embodiments, the modulating agents provided herein relate to a double-stranded oligonucleotide sequence, wherein only one of the two strands contains a non-natural nucleobase. In certain embodiments, the modulating agents as used herein relate to a double-stranded oligonucleotide sequence, wherein both of the strands independently comprise at least one non-natural nucleobase.

In certain instances, the ribose sugar moiety that naturally occurs in nucleosides is replaced with a hexose sugar. In certain aspects, the hexose sugar is an allose, altrose, glucose, mannose, gulose, idose, galactose, talose, or a derivative thereof. In a preferred embodiment, the hexose is a D-hexose. In certain instances, the ribose sugar moiety that naturally occurs in nucleosides is replaced with a polycyclic heteroalkyl ring or cyclohexenyl group. In certain instances, the polycyclic heteroalkyl group is a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane. In certain embodiments, the backbone of the oligonucleotide has been modified to improve the therapeutic or diagnostic properties of the oligonucleotide compound. In certain embodiments, at least one of the bases or at least one of the sugars of the oligonucleotide has been modified to improve the therapeutic or diagnostic properties of the oligonucleotide compound. In instances when the oligonucleotide is double stranded, the two strands are complementary, partially complementary, or chimeric oligonucleotides.

Examples of modified RNAi agents envisioned for use in the methods of the present invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. Modified oligonucleotides that do not have a phosphorus atom in their intersugar backbone can also be considered to be oligonucleotides. Specific oligonucleotide chemical modifications are described below. It is not necessary for all positions in a given compound to be uniformly modified, and in fact more than one of the following modifications may be incorporated in a single oligonucleotide compound or even in a single nucleotide thereof.

Examples of modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents that teach the preparation of the above phosphorus atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Examples of modified internucleoside linkages or backbones that do not include a phosphorus atom therein (i.e., oligonucleotides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other examples of oligonucleotide mimetics, both the sugar and the internucleoside linkage, i.e., the backbone, of the nucleoside units may be replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

The present invention further encompasses oligonucleotides employing ribozymes. Synthetic RNA molecules and derivatives thereof that catalyze highly specific endoribonuclease activities are known as ribozymes. (See, generally, U.S. Pat. No. 5,543,508 to Haseloff et al., and U.S. Pat. No. 5,545,729 to Goodchild et al.) The cleavage reactions are catalyzed by the RNA molecules themselves. In naturally occurring RNA molecules, the sites of self-catalyzed cleavage are located within highly conserved regions of RNA secondary structure (Buzayan et al., Proc. Natl. Acad. Sci. U.S.A., 1986, 83, 8859; Forster et al., Cell, 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

In certain instances, the RNAi agents for use with the methods provided herein may be modified by non-ligand group. A number of non-ligand molecules have been conjugated to oligonucleotides in order to enhance the activity, cellular distribution, cellular targeting, or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Additional examples of modulating agents, such as RNAi oligonucleotides, may be found in U.S. Application Publication Nos. 2007/0275465, 2007/0054279, 2006/0287260, 2006/0035254, 2006/0008822, which are incorporated by reference.

Peptide Transporters

In certain embodiments, the antisense compounds described herein may include an oligonucleotide moiety conjugated to a cell-penetrating peptide that enhances uptake of the oligonucleotide into a selected cell. Examples of such cells include T-cells, such as activated T-cells and quiescent T-cells. In certain embodiments, the antisense compounds of the invention may include an oligonucleotide moiety conjugated to an arginine-rich peptide transport moiety effective to enhance transport of the compound into cells.

In certain embodiments, the transport moiety is attached to a terminus of the oligomer, as illustrated, for example, in FIGS. 2A and 2B. In certain embodiments, the transport moiety is attached to the 5'-terminus of the oligomer. In certain embodiments, the transport moiety is attached to the 3-terminus of the oligomer.

In certain embodiments, the peptide transport moiety comprises about 6 to 16 subunits selected independently from X' subunits, Y' subunits, and Z' subunits, where (a) each X' subunit independently represents lysine, arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral amino acid —C(O)—$(CHR)_n$—NH—, where n is 2 to 7 and each R is independently H or methyl; and (c) each Z' subunit independently represents an α-amino acid having a neutral aralkyl side chain;

wherein the peptide comprises a sequence represented independently by any one or more of $(X'Y'X')_p$, $(X'Y')_m$, and $(X'Z'Z')_p$, where p is 2 to 5 and m is 2 to 8. Certain embodiments include various combinations selected independently from $(X'Y'X')_p$, $(X'Y')_m$, and/or $(X'Z'Z')_p$, including, for example, peptides having the sequence (X'Y'X')(X'Z'Z')(X'Y'X')(X'Z'Z') (SEQ ID NO:37).

In selected embodiments, for each X', the side chain moiety is guanidyl, as in the amino acid subunit arginine (Arg). In further embodiments, each Y' is —CO—$(CH_2)_n$—CHR—NH—, where n is 2 to 7 and R is H. For example, when n is 5 and R is H, Y' is a 6-aminohexanoic acid subunit, abbreviated herein as Ahx; when n is 2 and R is H, Y' is a β-alanine subunit, abbreviated herein as B. Certain embodiments relate to carrier peptides having a combination of different neutral amino acids, including, for example, peptides comprising the sequence -RahxRRBRRAhxRRBRAhxB- (SEQ ID NO:9), which contains both β-alanine and 6-aminohexanoic acid.

Certain peptides of this type include those comprising arginine dimers alternating with single Y' subunits, where Y' is preferably Ahx. Examples include peptides having the formula $(RY'R)_p$ or the formula $(RRY')_p$, where Y' is preferably Ahx. In one embodiment, Y' is a 6-aminohexanoic acid subunit, R is arginine and p is 4.

Certain embodiments include various linear combinations of at least two of $(RY'R)_p$ and $(RRY')_p$, including, for example, illustrative peptides having the sequence (RY'R)(RRY')(RY'R)(RRY') (SEQ ID NO:38), or (RRY')(RY'R)(RRY') (SEQ ID NO:39). Other combinations are contemplated. In a further embodiment, each Z' is phenylalanine, and m is 3 or 4.

In certain embodiments, the conjugated peptide is linked to a terminus of the oligomer via a linker Ahx-B, where Ahx is a 6-aminohexanoic acid subunit and B is a β-alanine subunit, as shown, for example, in FIGS. 2A and 2B.

In certain embodiments, for each X', the side chain moiety is independently selected from the group consisting of guanidyl (HN=C($NH_2$)NH—), amidinyl (HN=C($NH_2$)C<), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

In certain embodiments, the Y' subunits may be either contiguous, in that no X' subunits intervene between Y' subunits, or interspersed singly between X' subunits. In certain embodiments, the linking subunit may be between Y' subunits. In one embodiment, the Y' subunits are at a terminus of the transporter; in other embodiments, they are flanked by X' subunits. In further preferred embodiments, each Y' is —CO—$(CH_2)_n$—CHR—NH—, where n is 2 to 7 and R is H. For example, when n is 5 and R is H, Y' is a 6-aminohexanoic acid subunit, abbreviated herein as Ahx.

In certain embodiments of this group, each X' comprises a guanidyl side chain moiety, as in an arginine subunit. Certain peptides of this type include those comprising arginine dimers alternating with single Y' subunits, where Y' is preferably Ahx. Examples include peptides having the formula $(RY'R)_4$ or the formula $(RRY')_4$, where Y' is preferably Ahx. In the latter case, the nucleic acid analog is preferably linked to a terminal Y' subunit, preferably at the C-terminus, as shown, for example, in FIGS. 2A and 2B. The preferred linker is of the structure AhxB, where Ahx is a 6-aminohexanoic acid subunit and B is a β-alanine subunit.

The transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake is preferably evidenced by at least a two-fold increase, and preferably a four-fold increase, in the uptake of the compound into mammalian cells relative to uptake of the agent by an attached transport moiety lacking the hydrophobic subunits Y'. Uptake is preferably enhanced at least five-fold, ten-fold, twenty fold, and more preferably forty fold, relative to the unconjugated compound.

A further benefit of the transport moiety is its expected ability to stabilize a duplex between an antisense compound and its target nucleic acid sequence, presumably by virtue of electrostatic interaction between the positively charged transport moiety and the negatively charged nucleic acid. The number of charged subunits in the transporter is less than 14, as noted above, and preferably between 8 and 11, since too high a number of charged subunits may lead to a reduction in sequence specificity.

The use of peptide transporters such as arginine-rich peptide transporters (i.e., cell-penetrating peptides) are particularly useful in practicing the present invention. Certain peptide transporters have been shown to be highly effective at delivery of antisense compounds into primary leukocytes (Marshall, Oda et al. 2007). Furthermore, compared to other known peptide transporters such as Penetratin, the peptide transporters described herein, when conjugated to an antisense PMO, demonstrate an enhanced ability to alter splicing of several gene transcripts (Marshall, Oda et al. 2007). Especially preferred are the P007, CPO6062, and CPO4057 transport peptides listed below in Table 3 (SEQ ID NOS: 4, 9, and 10 respectively).

Exemplary peptide transporters, including linkers (B or AhxB) are given below in Table 3: Preferred sequences are those designated P007 (SEQ ID NO: 4) and CPO6062 (SEQ ID NO: 9).

TABLE 3

Exemplary Peptide Transporters for Intracellular Delivery of PMO

| Peptide | Sequence (N-terminal to C-terminal) | SEQ ID NO: |
|---|---|---|
| rTAT | RRRQRRKKRC | 1 |
| $R_9F_2$ | RRRRRRRRRFFC | 2 |
| $(RRAhx)_4B$ | RRAhxRRAhxRRAhxRRAhxB | 3 |
| $(RAhxR)_4AhxB$; (P007) | RAhxRRAhxRRAhxRRAhxRAhxB | 4 |
| $(AhxRR)_4AhxB$ | AhxRRAhxRRAhxRRAhxRRAhxB | 5 |
| $(RAhx)_6B$ | RAhxRAhxRAhxRAhxRAhxRAhxB | 6 |
| $(RAhx)_8B$ | RAhxRAhxRAhxRAhxRAhxRAhxRAhxB | 7 |
| $(RAhxR)_3AhxB$ | RAhxRAhxRRAhxRAhxB | 8 |
| $(RAhxRRBR)_2AhxB$; (CPO6062) | RAhxRRBRRAhxRRBRAhxB | 9 |
| $(RAhxR)5AhxB$ (CP04057) | RAhxRRAhxRRAhxRRAhxRRAhxRAhxB | 10 |

Contact Hypersensitivity and Methods of Use

Embodiments of the present invention include compositions and methods of treating or reducing skin or mucous membrane inflammation, including inflammation associated with contact hypersensitivity or contact dermatitis. These inflammatory conditions are typically associated with topical exposure to a sensitizing agent, such as an antigen. By way of non-limiting theory, activation-induced cell death (AICD) is a naturally occurring process for regulating the resolution of T-cell responses, and antisense targeting of cFLAR expression, alone or in conjunction with a selected antigen, sensitizes certain T-cells to undergo early AICD, resulting in tolerance to the sensitizing agent. Hence, in certain embodiments, the T-cells targeted by the antisense oligonucleotides described herein may be specific for or activated by one or more selected sensitizing agents, including foreign allergens and irritants, as compared to being specific for or activated by alloantigens or self-antigens.

As noted above, CFLAR expression can be targeted a variety of ways, such as by targeting the AUG start codon region or a splice region of a CFLAR mRNA transcript. Hence, certain embodiments include methods of inducing tolerance to a sensitizing agent, comprising topically applying an effective amount of an antisense composition containing an antisense oligonucleotide, wherein the antisense oligonucleotide targets the start site of a CFLAR mRNA or a splice site or branch point of a CFLAR mRNA. The antisense agent is typically effective to reduce expression of a functional human CFLAR in CFLAR-expressing lymphocytes, such as CD4+ and CD8+ T-cells. Also included are methods of treating contact hypersensitivity or contact dermatitis, comprising contacting the skin or mucous membrane of a subject with an effective amount of an antisense composition described herein.

Hypersensitivity relates to an undesirable reaction produced by the immune system, often in response to contact with a sensitizing agent such as an irritant or allergen. In a delayed type hypersensitivity reaction, CD8+ cytotoxic T cells and CD4+ helper T cells recognize sensitizing agents such as antigen in a complex with either type 1 or 2 major histocompatibility complex, and activate an undesired immune response, typically near the site of contact with the sensitizing agent. This process typically results in localized inflammation at the site of exposure to the agent, though certain reactions may produce a systemic reaction. Accordingly, certain embodiments include the treatment of hypersensitivity reactions, such as delayed type hypersensitivity reactions, mainly associated with a sensitizing agent.

Certain embodiments include the treatment or reduction of contact dermatitis, an inflammatory skin or mucous membrane reaction that results from exposure to sensitizing agents such as allergens (allergic contact dermatitis) or irritants (irritant contact dermatitis). Photocontact dermatitis occurs when the allergen or irritant is activated by sunlight Irritant dermatitis relates generally to inflammation that is triggered by contact with acids, alkaline materials such as soaps and detergents, solvents, adhesives, or other chemicals. The skin reaction in irritant dermatitis usually resembles a burn. Allergic contact dermatitis relates generally to inflammation that is triggered by exposure to a variety of different substances, typically a substance or material to which a subject is extra sensitive or allergic. The allergic reaction is often delayed, with the rash or other symptom appearing about 24-48 hours after exposure. The skin reaction in allergic dermatitis typically varies from mild irritation and redness to open sores, depending on the type of irritant, the body part affected, and the sensitivity of the individual.

Certain embodiments include the treatment of conditions related to dermatitis more generally. Examples of such conditions include psoriasis (i.e., a typically chronic, recurrent skin disease in humans marked by discrete macules, papules or patches covered with lamellated silvery scales resulting from an increased turnover of epidermal cells), seborrheic dermatitis, atopic dermatitis (eczema), thermal-induced dermatitis, drug-induced dermatitis, dyshidrotic dermatitis (i.e., a type of eczema that occurs on the palms of the hands, sides of the fingers, and soles of the feet, and typically causes a burning or itching sensation and a blistering rash), urticaria (i.e., a skin condition characterized by welts that itch intensely, caused by an allergic reaction, an infection, or a nervous condition; often called "hives"), and bullous dermatitis.

The symptoms of contact dermatitis include itching (pruritus) of the skin in exposed areas, redness or inflammation in the exposed area, tenderness of the skin in the exposed area, localized swelling of the skin, warmth of the exposed area, skin lesion or rash at the site of exposure, including redness, rash, papules (pimple-like), vesicles, and bullae (blisters). Also, the lesions may involve oozing, draining, or crusting, or may become scaly, raw, or thickened. The symptoms of contact dermatitis may last from several days to several weeks. Chronic contact dermatitis refers to inflammation that persists after removal of the offending sensitizing agent.

Contact hypersensitivity or dermatitis may occur on any body surface such as the skin or mucous membranes. Skin architecture is well known. Briefly, epidermis, the skin outer layer, is covered by the stratum corneum, a protective layer of dead epidermal skin cells (e.g., keratinocytes) and extracellular connective tissue proteins. The epidermis undergoes a continual process of being sloughed off as it is replaced by new material pushed up from the underlying epidermal granular cell, spinous cell, and basal cell layers, where continuous cell division and protein synthesis produce new skin cells and skin proteins (e.g., keratin, collagen). The dermis lies underneath the epidermis, and is a site for the elaboration by dermal fibroblasts of connective tissue proteins (e.g., collagen, elastin, etc.) that assemble into extracellular matrix and fibrous structures that confer flexibility, strength and elasticity to the skin. Also present in the dermis are nerves, blood vessels, smooth muscle cells, hair follicles and sebaceous glands. Included are skin sites such as the head, face, ears (e.g., otitis externa), neck, arms, hands, underarms, chest, back, pelvis, groin, buttocks, legs, and feet.

The mucous membranes (i.e., mucosae or mucosa) refer linings of mostly endodermal origin, covered in epithelium, which are involved in absorption and secretion. Mucous membranes line various body cavities that are exposed to the external environment, and are continuous with the skin at several places, including the nostrils, the lips, the ears, the eyes, the genital area, and the anus. Examples of mucosal membranes include the buccal mucosae (mucous membrane of the inside of the cheek), esophageal mucosae, gastric mucosae, intestinal mucosae, nasal mucosae, olfactory mucosae, oral mucosae, bronchial mucosae, uterine mucosae (e.g., endometrium), and penile mucosae. Also included are opthalmologic tissues. For instance, allergy to chemicals in opthalmologic preparations may provoke dermatitis around the eyes. Hence, certain embodiments relate to treating hypersensitivity or contact dermatitis associated with any one or more of these skin sites or mucosal sites, and may include application of an antisense composition to any one or more of these sites.

A sensitizing agent refers to any substance that causes a hypersensitivity or other inflammatory reaction in skin or mucosal membranes of a subject. In certain embodiments, the sensitizing agent causes contact dermatitis in the subject. Included are allergens and irritants, among others, such as haptens and hapten-protein conjugates. Particular examples of sensitizing agents include, without limitation, acids, alkalis (e.g., soaps, detergents, drain cleaners, strong soap with lye residues), solvents (e.g., alcohol, xylene, turpentine, esters, acetone, ketones), heavy metals (e.g., nickel, gold, cobalt such as cobalt chloride) rubber (e.g., mercaptobenzothiazole), latex, surfactants (e.g., sodium lauryl sulfate), kerosene, chlorine, ethylene oxide, cosmetics, antiseptics, insecticides, potassium dichromate (e.g., cements, household cleaners), paraphenylenediamine, certain dental products, formaldehyde, and fragrances (e.g., Myroxolon pereirae). Further examples of sensitizing agents include urushiol oil, medications (e.g., antibiotics such as neomycin and bacitracin, topical steroids, fungicides such as thiram), quaternium-15, and thimerosal, a mercury compound used in local antiseptics and in vaccines.

Also included are chromates, or compounds containing chromium, which can be found in cement, leather, some matches, paints and anti-rust compounds. Occupational exposure to chromium is common in jobs in the automobile, welding, foundry, cement, railroad and building repair industries.

In certain embodiments, contact dermatitis may result from exposure to plants, including plants that contain a sensitizing agent. Examples of plant-based sensitizing agents include a number of alkaloids, glycosides, saponins, anthraquinones, irritant calcium oxalate crystals, and urushiol oil. Examples of plants that contain urushiol oil include poison oak, poison ivy, poison sumac, and other Anacardiaceae plant family members or other plants that elicit similar inflammatory responses.

Also included is the treatment of contact dermatitis associated with low humidity. For instance, low humidity from air conditioning has been shown to cause irritant contact dermatitis, mainly due to the lack of sufficient water vapor.

Certain embodiments included treatment of photocontact dermatitis, or photoaggravated dermatitis. This type of dermatitis may be triggered by an interaction between an otherwise benign or less harmful substance (e.g., a sensitizing agent) and a source of ultraviolet light, such as the sun or a tanning bed lamp. Typically, the ultraviolet light is in the range of about 320-400 nm.

Certain embodiments include reducing the risk of secondary conditions or complications associated with contact dermatitis. For instance, the methods provided herein may reduce secondary bacterial skin infections that often occur during or following contact dermatitis.

Also included are combination therapies. For instance, the antisense oligonucleotides described herein may be combined with one or more standard treatment agents or modalities. Examples of standard treatment agents include calamine lotion, steroids such as corticosteroids (e.g., hydrocortisone cream), antihistamines, and barrier creams such as creams that contain zinc oxide. Included are compositions that comprise an antisense agent and at least one of these standard treatment agents, as well as methods of combination therapy using said treatment agents, whether by applying them sequentially with or at the same time as the antisense agent.

In certain embodiments, antisense oligonucleotides may be administered simultaneously, separately, or over a period of time in association with one or several allergens. Administration includes applying the composition to the affected area skin or mucous membrane area or area at risk of exposure to the agent, and rubbing the composition into the skin or mucous membrane. Application may be once a day or less often, or two or more times a day, e.g., every 8 hours. In certain embodiments, the administration of the pharmaceutical composition and the allergen will be localized. In another embodiment, the allergen is a component of the pharmaceutical composition.

The time course of administration may be similar to current allergen desensitization treatment regimens. For illustration only, the treatment regimen may range from a single treatment to daily treatments for one to 12 weeks or until the clinical criteria for contact dermatitis has been resolved. In certain embodiments, the composition may be applied to a skin area of the subject prior to contact with the sensitizing agent. In certain embodiments, the composition may be applied to a skin area of the subject at the same time as the sensitizing agent. In certain embodiments, the composition may be applied to a skin area of the subject after contact with the sensitizing agent.

Topical Compositions

Also included are pharmaceutical compositions or formulations that comprise the CFLAR-targeted antisense agents described herein. In certain embodiments, the pharmaceutical compositions are adapted for topical administration, and include compositions suitable for application to skin or mucous membranes.

The step of administering may be performed by any means known to the art, for example, topically, transdermally, sublingually, subcutaneously, transbuccally, intranasally, via inhalation, and intraoccularly. In preferred embodiments administering may be performed topically, where pharmaceutical excipients or carriers for topical use are described herein and known in the art. Certain other embodiments contemplate administration of the formulations described herein as a bulk deposition, which may be, for example time-released or alternatively immediately available As noted above, certain invention embodiments described herein relate to topical formulations of the described antisense oligonucleotides, which formulations comprise the oligonucleotides in a pharmaceutically acceptable carrier, excipient or diluent and in a therapeutic amount, as disclosed herein, when administered topically to an animal, preferably a mammal, and most preferably a human.

Topical administration of the oligonucleotides described herein, or their pharmaceutically acceptable salts, in pure form or in an appropriate pharmaceutical composition, can be carried out via any of the accepted modes of topical administration of agents for serving similar utilities. Topical application or administration of a composition means, in preferred embodiments, directly contacting the composition (e.g., a topical formulation) with skin or mucosa of the subject undergoing treatment, which may be at one or more localized or widely distributed skin or mucosal sites and which may generally refer to contacting the topical formulation with intact stratum corneum or epidermis but need not be so limited; for instance, certain embodiments contemplate as a topical application the administration of a topical formulation described herein to injured, abraded, wrinkled or damaged skin (including photodamaged skin), or skin of a subject undergoing surgery, such that contact of the topical formulation may take place not only with stratum corneum or epidermis but also with skin granular cell, spinous cell, and/or basal cell layers, and/or with dermal or underlying tissues, for example, as may accompany certain types of skin tissue remodeling.

The topical formulations with an appropriate pharmaceutically acceptable carrier, diluent or excipient for use in a topical formulation preparation, and may be formulated into preparations in solid, semi-solid, gel, cream, colloid, suspension or liquid or other topically applied forms, such as powders, granules, ointments, solutions, washes, gels, pastes, plasters, paints, bioadhesives, microsphere suspensions, and aerosol sprays. Pharmaceutical compositions of these and related embodiments are formulated so as to allow the active ingredients contained therein to be bioavailable upon topical administration of the composition to skin of a subject, such as a mammal, including a human.

Depending on the particular embodiments, which may vary as will be appreciated by the skilled artisan in part as a function of the condition to be treated in a given subject, the topical formulations described herein deliver a therapeutically effective amount of, e.g., the antisense oligonucleotides or other active compound(s) to skin cells such as epithelial cells, keratinocytes, cells of the scalp (including in certain embodiments cells such as follicular cells and/or melanocytes), dermal fibroblasts, and/or mucosal tissue. Preferred formulations may exhibit ready permeability into the skin or mucosa, as can be determined according to any of a number of established methodologies known to the art for testing the skin or mucosal permeability of a drug composition (see, e.g., Wagner et al., 2002 *J. Invest. Dermatol.* 118:540, and references cited therein; Bronaugh et al., 1985 *J. Pharm. Sci.* 74:64; Bosman et al., 1998 *J. Pharm. Biomed. Anal.* 17:493-499; Bosman et al., 1996 *J. Pharm Biomed Anal.* 1996 14:1015-23; Bonferoni et al., 1999 *Pharm Dev Technol.* 4:45-53; Frantz, Instrumentation and methodology for in vitro skin diffusion cells in methodology for skin absorption. In: Methods for Skin Absorption (Kemppainen & Reifenrath, Eds), CRC Press, Florida, 1990, pp. 35-59; Tojo, Design and calibration of in vitro permeation apparatus. In: Transdermal Controlled Systemic Medications (Chien Y W, Ed), Marcel Dekker, New York, 1987, 127-158; Barry, Methods for studying percutaneous absorption. In: Dermatological Formulations: Percutaneous absorption, Marcel Dekker, New York, 1983, 234-295).

Compositions that will be administered to the skin of a subject may in certain embodiments take the form of one or more dosage units, where for example, a liquid-filled capsule or ampule may contain a single dosage unit, and a container of a topical formulation as described herein in aerosol form may hold a plurality of dosage units. Methods of preparing such dosage forms are known to those skilled in the art; for example, see The Science and Practice of Pharmacy, 20th Edition (Philadelphia College of Pharmacy and Science, 2000). The composition to be administered may contain an effective amount of a CFLAR-targeted antisense oligonucleotide or a pharmaceutically acceptable salt thereof, as described herein.

As noted above, the present topical formulations may take any of a wide variety of forms, and include, for example, creams, lotions, solutions, sprays, gels, ointments, pastes or the like, and/or may be prepared so as to contain liposomes, micelles, and/or microspheres. See, e.g., U.S. Pat. No. 7,205, 003. For instance, creams, as is well known in the arts of pharmaceutical and cosmeceutical formulation, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semi-liquid preparations in which solid particles, including the active agent, are present in a water or alcohol base. Lotions are usually suspensions of solids, and preferably comprise a liquid oily emulsion of the oil-in-water type. Lotions are preferred formulations herein for treating large body areas, because of the ease of applying a more fluid composition. It is generally preferred that the insoluble matter in a lotion be finely divided. Lotions typically contain suspending agents to produce better dispersions as well as compounds useful for localizing and holding the active agent in contact with the skin or mucosa, e.g., methylcellulose, sodium carboxymethyl-cellulose, or the like.

Solutions refer to homogeneous mixtures prepared by dissolving one or more chemical substances (solutes) in a liquid such that the molecules of the dissolved substance are dispersed among those of the solvent. The solution may contain other pharmaceutically acceptable and/or cosmeceutically acceptable chemicals to buffer, stabilize or preserve the solute. Common examples of solvents used in preparing solutions are ethanol, water, propylene glycol or any other pharmaceutically acceptable and/or cosmeceutically acceptable vehicles.

Gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred "organic macromolecules," i.e., gelling agents, may be chemically crosslinked polymers such as crosslinked acrylic acid polymers, for instance, the "carbomer" family of polymers, e.g., carboxypolyalkylenes, that may be obtained commercially under the Carbopol® trademark. Also preferred in certain embodiments may be hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: *The Science and Practice of Pharmacy,* 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight (see, e.g., Remington, Id.).

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having one (unilamellar) or a plurality (multilamellar) of lipid walls comprising a lipid bilayer, and, in the present context, may encapsulate and/or have adsorbed to their lipid membranous surfaces one or more components of the topical formulations herein described, such as the antisense oligonucleotides certain carriers or excipients. Liposomal preparations herein include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl-8 dodecyl ether, polyoxyl-12 dodecyl ether, nonoxynol 10, and nonoxynol 30. Microspheres, similarly, may be incorporated into the presently described topical formulations.

Like liposomes and micelles, microspheres essentially encapsulate one or more components of the present formulations. They are generally, but not necessarily, formed from lipids, preferably charged lipids such as phospholipids. Preparation of lipidic microspheres is well known in the art.

Various additives, as known to those skilled in the art, may also be included in the topical formulations. For example, solvents, including relatively small amounts of alcohol, may be used to solubilize certain formulation components. It may be desirable, for certain topical formulations or in cases of particularly severe inflammatory conditions of the skin, to include in the topical formulation an added skin permeation enhancer in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer® (231, 182, 184), Tween® (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine, and triethanolamine; terpenes; alkanones; and organic acids, particularly citric acid and succinic acid. Azone® and sulfoxides such as DMSO and $C_{10}MSO$ may also be used, but are less preferred.

Certain skin permeation enhancers include lipophilic co-enhancers typically referred to as "plasticizing" enhancers, i.e., enhancers that have a molecular weight in the range of about 150 to 1000 daltons, an aqueous solubility of less than about 1 wt %, preferably less than about 0.5 wt %, and most preferably less than about 0.2 wt %. The Hildebrand solubility parameter of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents. Additional skin permeation enhancers will be known to those of ordinary skill in the art of topical drug delivery, and/or are described in the relevant literature. See, e.g., *Percutaneous Penetration Enhancers*, eds. Smith et al. (CRC Press, 1995).

Various other additives may be included in the topical formulations according to certain embodiments of the present invention, in addition to those identified above. These include, but are not limited to, antioxidants, astringents, perfumes, preservatives, emollients, pigments, dyes, humectants, propellants, and sunscreen agents, as well as other classes of materials whose presence may be cosmetically, medicinally or otherwise desirable. Typical examples of optional additives for inclusion in the formulations of the invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), $\alpha$-tocopherol (Vitamin E), $\beta$-tocopherol, $\gamma$-tocopherol, $\delta$-tocopherol, $\epsilon$-tocopherol, $\zeta_1$-tocopherol, $\Lambda_2$-tocopherol, $\eta$-tocopherol, and retinol (vitamin A); essential oils, ceramides, essential fatty acids, mineral oils, vegetable oils (e.g., soy bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that may be obtained commercially under the Carbopol® trademark.

Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Other advantageously included cosmeceutically active agents may be present, for example, $\alpha$-hydroxyacids, $\alpha$-ketoacids, polymeric hydroxyacids, moisturizers, collagen, marine extracts, and antioxidants such as ascorbic acid (vitamin C), $\alpha$-tocopherol (Vitamin E) or other tocopherols such as those described above, and retinol (vitamin A), and/or cosmetically acceptable salts, esters, amides, or other derivatives thereof. Additional cosmetic agents include those that are capable of improving oxygen supply in skin tissue, as described, for example, in WO 94/00098 and WO 94/00109. Sunscreens may also be included.

Other embodiments may include a variety of non-carcinogenic, non-irritating healing materials that facilitate treatment with the formulations of the invention. Such healing materials may include nutrients, minerals, vitamins, electrolytes, enzymes, herbs, plant extracts, glandular or animal extracts, or safe therapeutic agents that may be added to the formulation to facilitate dermal healing. The amounts of these various additives are those conventionally used in the cosmetics field, and range, for example, from about 0.01% to about 20% of the total weight of the topical formulation.

The formulations of the invention may also include conventional additives such as opacifiers, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from methyl and propyl esters of p-hydroxybenzoic acid (e.g., methyl and propyl paraben), sodium benzoate, sorbic acid, imidurea, and combinations thereof. The formulations may also contain irritation-mitigating additives to minimize or eliminate the possibility of skin irritation or skin damage resulting from the skin tissue repair-promoting compound to be administered, or from other components of the composition. Suitable irritation-mitigating additives include, for example: $\alpha$-tocopherol; monoamine oxidase inhibitors, particularly phenyl alcohols such as 2-phenyl-1-ethanol; glycerin; salicylates; ascorbates; ionophores such as monensin; amphiphilic amines; animonium chloride; N-acetylcysteine; capsaicin; and chloroquine. The irritation-mitigating additive, if present, may be incorporated into the topical formulation at a concentration effective to mitigate irritation or skin damage, typically representing not more than about 20 wt %, more typically not more than about 5 wt %, of the formulation.

In certain embodiments, a topical composition may include any normally used galenic formulation, such as an aqueous, hydroalcoholic or oily solution, an oil-in-water or water-in-oil or multiple emulsion, an aqueous or oily gel, a liquid, paste or solid anhydrous product, an oil dispersion in a polymeric phase such as nanospheres and nanocapsules and/or non-ionic type lipidic vesicles. Such compositions may be more or less fluid and may be in the form of a white or colored cream, a pomade, a milk, a lotion, a serum, a paste or a foam. It may even be applied on the skin in the form of an aerosol. It may also be in powder or other solid form, for example in stick form. Such compositions may also be in the form of patches, pencils, brushes or applicators used for local application on spots on the face or hands. The compositions provided herein may also contain additives normally used in the cosmetic field, such as hydrophilic or lipophilic gels, hydrophilic or lipophilic active constituents, preservation agents, antioxidants, solvents, odorants, fillers, filters, pigments, odor absorbers and coloring material. The quantities of these different additives are as conventionally used in the fields considered. Depending on the nature, these additives may be added in the fatty phase, in the aqueous phase, in lipidic vesicles and/or in nanoparticles.

In one embodiment of the invention, the pharmaceutical composition is in the form of an emulsion containing an oil, an emulsifier chosen from among fatty acid and polyethylene glycol esters such as PEG-20 stearate, and fatty acid and glycerine esters such as glycerine stearate, and a co-emulsifier. When the cosmetic composition of the invention is an emulsion, the proportion of the fatty phase can vary from 5 to 80% by weight, and preferably from 5 to 50% by weight with reference to the total weight of the composition. The oils, emulsifiers and co-emulsifiers used in the composition in emulsion form are chosen from among those conventionally used in the field considered. The emulsifying agent and the co-emulsifying agent are present in the composition in a proportion varying from 0.3% to 30% by weight, and preferably from 0.5% to 20% by weight compared with the total weight of the composition. Oils that can be used in association with oligomer conjugates according to the invention include mineral oils (Vaseline oil), vegetable origin oils (avocado oil, Soya oil), animal origin oils (lanoline), synthetic oils (perhydrosqualene), silicone oils (cyclomethicone) and fluorine oils (perfluoropolyethers). Fatty alcohols (cetylic alcohol), fatty acids, waxes (Carnauba wax, ozokerite) can also be used as fatty materials. For example, emulsifiers and coemulsifiers that can be used in association with oligomer conjugates according to the invention include fatty acid and polyethylene glycol esters such as PEG-20 stearate and fatty acid and glycerine esters such as glyceryl stearate. Hydrophilic gelifiers that can be used in association with oligomer conjugates according to the invention include in particular carboxyvinylic polymers (carbomer), acrylic copolymers such as acrylate/alkylacrylate copolymers, polyacrylamides, polysaccharides, natural gums and clays. Lipophilic gelifiers include modified clays like bentones, metallic salts of fatty acids, hydrophobic silica and polyethylenes.

Antisense oligonucleotides for use in the present formulations, or their pharmaceutically acceptable salts, are administered in an effective amount, which will vary depending upon a variety of factors including the activity of the specific oligonucleotide employed; the metabolic stability and length of action of the oligonucleotide; the age, body weight, general health, sex, skin type and diet of the subject; the mode and time of administration; the rate of excretion; the drug combination; the severity of the particular inflammatory condition for which treatment is desired; and the subject undergoing therapy. In certain embodiments, an effective or therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g). In certain embodiments, treatment is characterized in that the antisense oligomer or conjugate thereof represent(s) 0.0001% to 10%, preferably 0.003% to 3% of the total weight of the topical pharmaceutical composition.

The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., The Merck Manual, 16$^{th}$ edition, Merck and Co., Rahway, N.J., 1992; Goodman et al., eds., Goodman and Gilman's The Pharmacological Basis of Therapeutics, 10$^{th}$ edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18$^{th}$ edition, Mack Publishing Co., Easton, Pa. (1990); Katzung, Basic and Clinical Pharmacology, Appleton and Lange, Norwalk, Conn. (1992)).

The total dose required for each treatment can be administered by multiple doses or in a single dose over the course of the day, if desired. Certain preferred embodiments contemplate a single administration of the formulation per day. Generally, and in distinct embodiments, treatment may be initiated with smaller dosages, which are less than the optimum dose of the oligonucleotide. Thereafter, the dosage may be increased by small increments until the optimum effect under the circumstances is reached.

The compositions described herein can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, Regional Anesthesia 22 (6): 543-551 (1997), all of which are incorporated herein by reference.

The most suitable route will depend on the nature and severity of the condition being treated. Those skilled in the art are also familiar with determining topical administration methods (sprays, creams, open application, occlusive dressing, soaks, washes, etc.), dosage forms, suitable pharmaceutical excipients and other matters relevant to the delivery of the oligonucleotides to a subject in need thereof.

All of the U.S. patents, U.S. patent applications, foreign patents, foreign patent applications, and non-patent applications referred to in this specification and/or listed in the Application Data Sheet are incorporated herein by reference in their entirety.

The following Examples are presented by way of illustration and not limitation.

EXAMPLES

The following examples illustrate the method of the invention in reducing skin inflammation when topically applied in a contact hypersensitivity model.

They are presented to further illustrate and explain the present invention and should not be taken as limiting in any regard.

Materials and Methods

Peptide-conjugated PMO (PPMO) synthesis_A PMO targeting the AUG translation initiation sequence of murine CFLAR (SEQ ID NO:28) and a scrambled control sequence (SEQ ID NO:35) were synthesized at AVI BioPharma (Corvallis, Oreg.). Purity of full length oligomers was >95% as determined by reverse-phase high-pressure liquid chromatography (HPLC) and MALDI TOF mass spectroscopy. Peptide-conjugated PMO (PPMO) were produced by attaching the carboxy terminal cysteine of the peptide R9F2 (SEQ ID NO:2) to the 5' end of the CFLAR and Scrambled control PMOs through a cross-linker N-[α-maleimidobutyryloxy] succinimide ester (BGBS). The lyophilized PPMOs (SEQ ID NOS:28 and 35) were dissolved in sterile $H_2O$ prior to use in cell cultures, dissolved in PBS prior to intraperitoneal (i.p.) injection in mice, or dissolved in sterile $H_2O$ or 95% propylene glycol/5% linoleic acid prior to topical administration on mice ear skin.

Mice. BALB/c and D0.11 mice 6-12 weeks of age were obtained from Simonsen or Charles River laboratories and housed in micro-isolator cages 3-5 per cage during acclimatization and treatment periods. Animals were exposed to a 12-hr light/dark cycle in a temperature- and humidity-controlled environment and allowed access to commercially available pre-autoclaved sterilized rodent diet and autoclaved sterilized water. Temperature controls were set to maintain temperatures at 18° to 26° C. Autoclaved caging, water bottles and storage containers were used to avoid exposure of animals to any contaminated materials.

Contact hypersensitivity model. On day 0 the bellies of BALB/c mice were shaved using a small animal clipper (Oster, 40) and mice were sensitized by pipeting either 20 uL of 0.5% FITC diluted 4:1 acetone/dibutyl phthalate or 2% oxazolone (4-ethoxymethylene-2-phenyl-2-oxazolin-5) diluted in 4:1 acetone/olive oil onto the shaved region. On day 5 animals were pre-treated with 20 uL of cFLAR PPMO (SEQ ID NO: 28) or scrambled sequence PPMO (SEQ ID NO: 35) dissolved in 95% propylene glycol and 5% linoleic acid, and applied topically to an area of the animal to be tested, in the present method, to each side of one ear. On day 6 mice were similarly pretreated by topical administration of PMO. Approximately 15 minutes later, an eliciting dosage of either 10 uL of 0.2% FITC diluted 4:1 acetone/dibutyl phthalate or 1% oxazolone in 4:1 acetone/olive oil was epicutaneously applied to each side of the treated ear. Twenty four hours later ear thickness measurements were taken on both ears using a Starrett Caliper (#1015 MH, Athol, Mass.). Each reading was performed three times and the median value was used for all analysis.

In a second study, the memory response was tested by giving a second eliciting dose. On day 21, 15 days after the initial elicitation, animals were treated with either 10 uL of 0.2% FITC in 4:1 acetone/dibutyl phthalate or 1% oxazolone in 4:1 acetone/olive, epicutaneously applied to each side of the opposite ear. On day 26, five days after second eliciting dose, the thickness of each ear was measured using caliper. Right and left ears were both measured as described earlier. Animals were euthanized, ears were removed and placed into 10% buffered formalin solution for 24 hours for paraffin embedding, sectioning, H&E staining and immunohistochemistry. The differences between thickness of treated and untreated ears for each mouse were determined. The mean and the standard error were then calculated and Analysis of Variance followed by a Newman-Keuls Post test was performed with significance set at p<0.05 using GraphPad Prism (GraphPad, San Diego, Calif.).

Example 1

Inhibition of CFLAR Long and Short Isomer Protein Expression in Activated T Cells with CFLAR PPMO The effect of an AUG targeted CFLAR PPMO on protein expression of CFLAR long ($CFLAR_L$) and short ($CFLAR_S$) isoforms in activated T cells was determined in vitro. The $CFLAR_L$ and $CFLAR_S$ proteins are isoforms of CFLAR which share the same translation initiation sequence within the mature mRNA and are therefore both complementary with the AUG targeted CFLAR PPMO. Purified BALB/c splenic T cells were cultured with plate bound anti-CD3 [5 µg/ml] and treated with 5 µM CFLAR PPMO (SEQ ID NO: 28), scrambled control sequence PPMO (SEQ ID NO: 35), or no treatment and analyzed for CFLAR long ($cFLAR_L$) and short (CFLARs) isomer protein expression after 24 hours.

Figure 3:
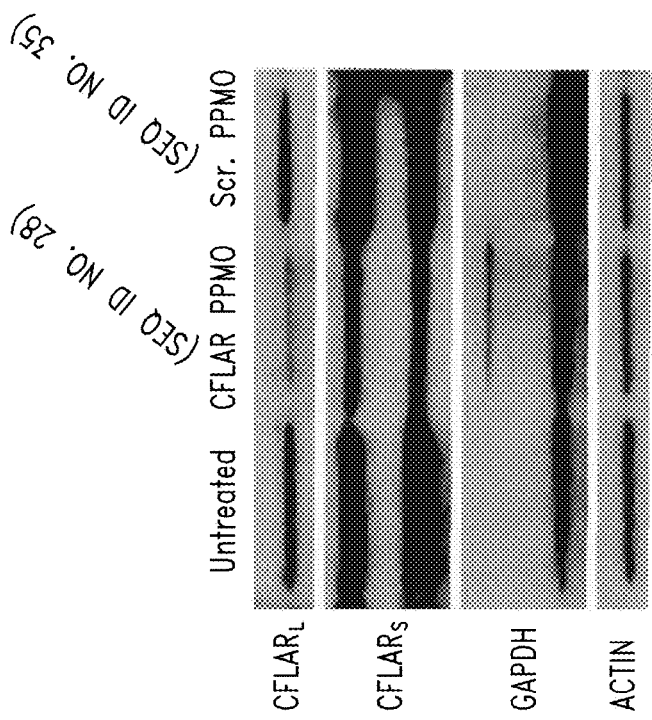
FIG. 3 shows inhibition of CFLAR protein expression and detection of a higher molecular weight stress-induced insoluble aggregate of GAPDH in activated T cells treated with CFLAR PPMO (SEQ ID NO: 28)

Immunoblot analysis revealed diminished levels of both $CFLAR_L$ and $CFLAR_S$ protein in cells treated with CFLAR PPMO while scrambled control PPMO treatment and untreated cells showed no effect (FIG. 3). In addition, cells treated with CFLAR PPMO displayed a higher molecular weight band in the GAPDH immunoblot not present in scrambled PPMO treated or untreated cells, which may be indicative of stress-induced insoluble aggregation of GAPDH in cells undergoing activation-induced cell death due to CFLAR antisense blockade (FIG. 3). Although such results have not previously been described for cultured T cells, it has been shown in cultured nerve cells that formation of an oxidative stress-induced insoluble aggregate of GAPDH due to intermolecular disulfide bonding is visible as a high molecular weight GAPDH band (Nakajima et al., 2007, *J. Biol. Chem.* 282:26562-74).

Example 2

Antigen-Specific Induction of Apoptosis in T Cells with CFLAR PPMO

Evidence of antigen-specific activation induced cell death (AICD) in ovalbumin-specific CD4+ T cells treated with cFLAR PPMO was examined in vitro. Freshly isolated splenocytes from ovalbumin-specific T cell receptor (TCR) transgenic (DO.11) mice were treated with 2.5 µM CFLAR PPMO (SEQ ID NO: 28), scrambled control PPMO (SEQ ID NO: 35) or media control overnight then co-cultured with BALB/c bone marrow derived lipopolysaccharide (Ips) matured ovalbumin pulsed DCs or control Ips stimulated DCs for 24 hours. Apoptotic indicators were then examined by flow cytometry using propidium iodide with anti-TCR KJ26+ staining to examine loss of cell membrane integrity in KJ26+ cells and using a caspase-3 fluorescing substrate to examine caspase activation.

Antigen-specific activated T cells treated with CFLAR PPMO displayed a marked affect on apoptotic indicators as evidenced by decreased membrane integrity and caspase activation versus activated T cells treated with scrambled control PPMO or non-activated T cells treated with CFLAR PPMO (data not shown).

Example 3

Inhibition of FITC-Induced Dermatitis with Topical Application of CFLAR PPMO

Contact hypersensitivity responses induced in mice by epicutaneous application of fluorescein isothiocyanate (FITC) were examined to determine if topical application of CFLAR PPMO could reduce skin inflammation. The delayed-type hypersensitivity (DTH) response was first tested in FITC pre-sensitized mice followed by topical administration of 3, 30, 300 and 3000 µg/ear of CFLAR PPMO (SEQ ID NO: 28), 300 µg/ear scrambled control PPMO (SEQ ID NO: 35), or 95% propylene glycol/5% linoleic acid vehicle alone to both ears for two days followed immediately by an eliciting dosage of FITC applied to each side of one ear (N=6-9 per treatment group). Both ears were measured 24 hours later and the difference between thickness of FITC treated and untreated ears for each mouse was determined. The memory response was then tested 15 days later with a second eliciting dose of FITC applied to each side of the opposite ear followed by right and left ear thickness measurements five days later. Treatment effectiveness was compared to ears from FITC sensitized mice not receiving topical PPMO or vehicle alone. Mice were euthanized for removal of ears for examination of leukocyte infiltration and CFLAR protein via H&E staining and immunohistochemistry, respectively.

Figure 4A:
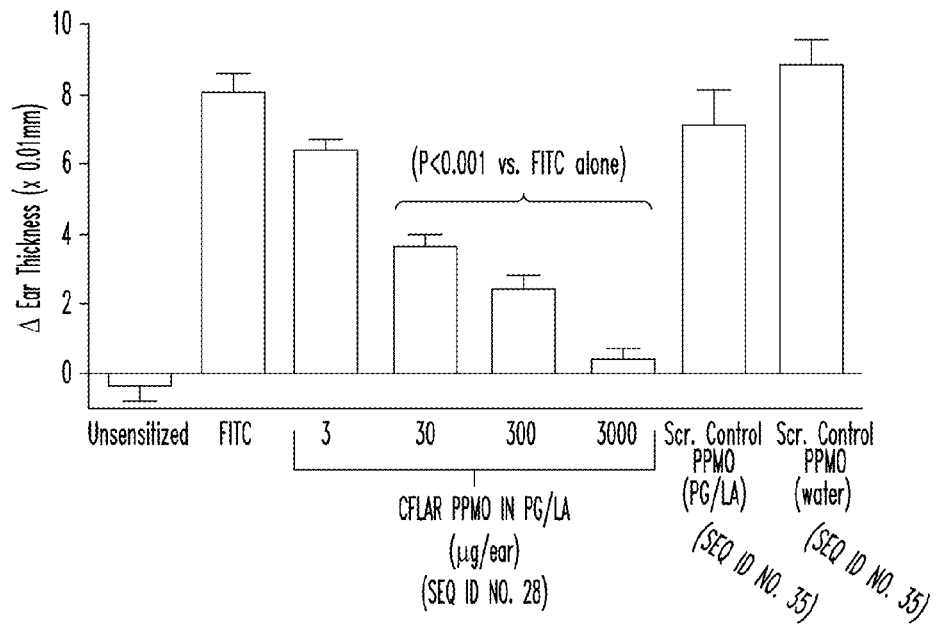
FIGS. 4A and 4B show inhibition of FITC-induced dermatitis in mice with topically applied CFLAR PPMO. Topical application of CFLAR PPMO (SEQ ID NO: 28) caused a dose-dependent inhibition of initial FITC-induced DTH (FIG. 4A) and FITC-induced memory response at 15 days post initial FITC challenge and topical application of CFLAR PPMO (FIG. 4B).

Ear thickness measurements demonstrated that topical CFLAR PPMO reduced FITC induced DTH in a dose dependent manner, with topical 3, 30, 300 and 3000 µg/ear dosages causing a 21%, 57%, 70% and 96% decrease in ear thickening, respectively (p<0.001 for 30, 300 and 3000 µg/ear treatment groups), versus FITC sensitization alone. Topical scrambled control PPMO and vehicle alone treatments caused a non-significant 12% and 17% reduction, respectively (FIG. 4A).

Figure 4B:
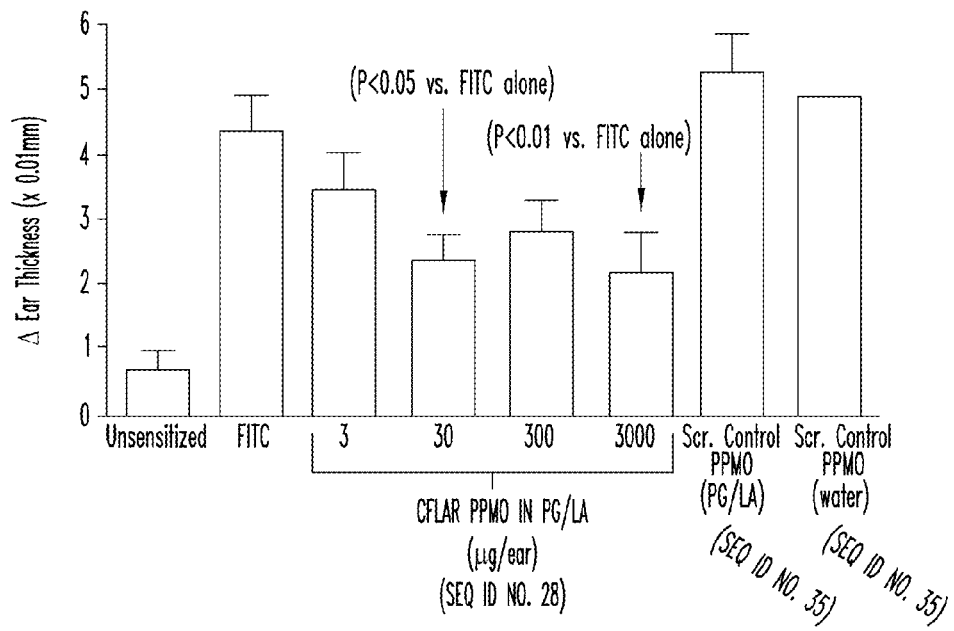

Memory response after the second FITC challenge given 15 days later showed less of a CFLAR PPMO dose response effect versus the effect on the first FITC challenge, although the second FITC challenge generated a smaller change in ear thickness versus the first challenge (0.043 versus 0.08 mm) in controls. Mice receiving the 3, 30, 300, and 3000 µg/ear CFLAR PPMO treatments 15 days earlier displayed a 23%, 47% (p<0.05), 35% (p>0.05), and 54% (p<0.01) decrease in ear thickening, respectively, versus FITC sensitization alone (FIG. 4B).

Figure 5A:
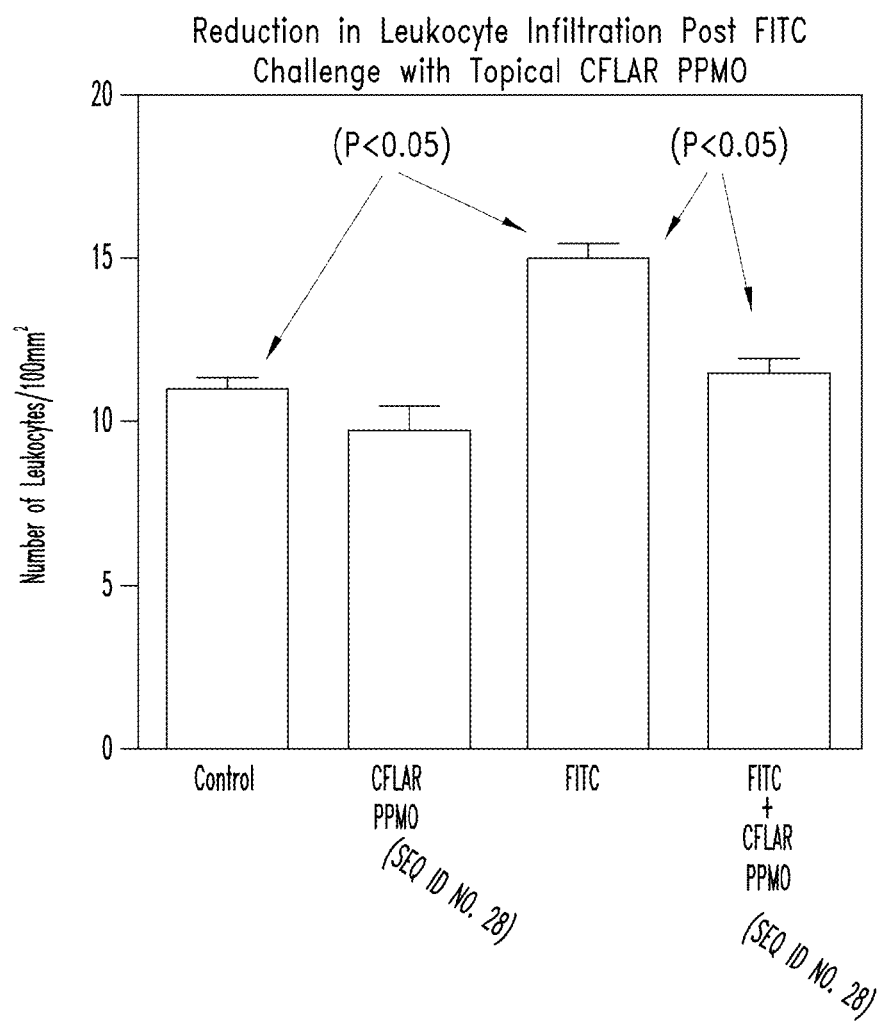
FIGS. 5A-5E show reduction of leukocyte numbers as illustrated by a plot (FIG. 5A) and as seen by histological examination in (FIGS. 5B-5E) under various treatment conditions.
Figure 5B:
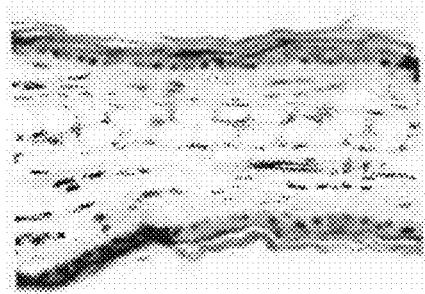
Figure 5C:
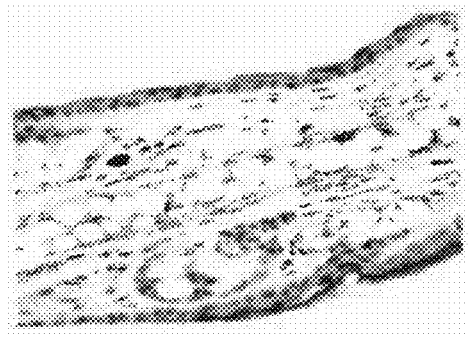
Figure 5D:
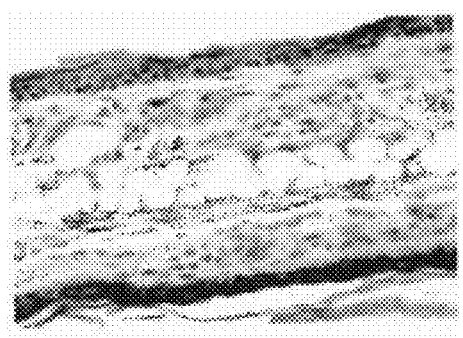
Figure 5E:
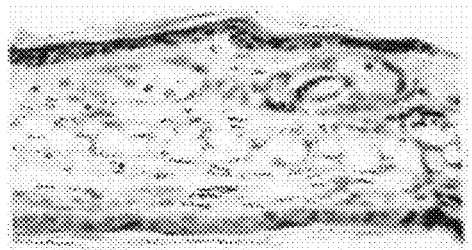
Figure 6:
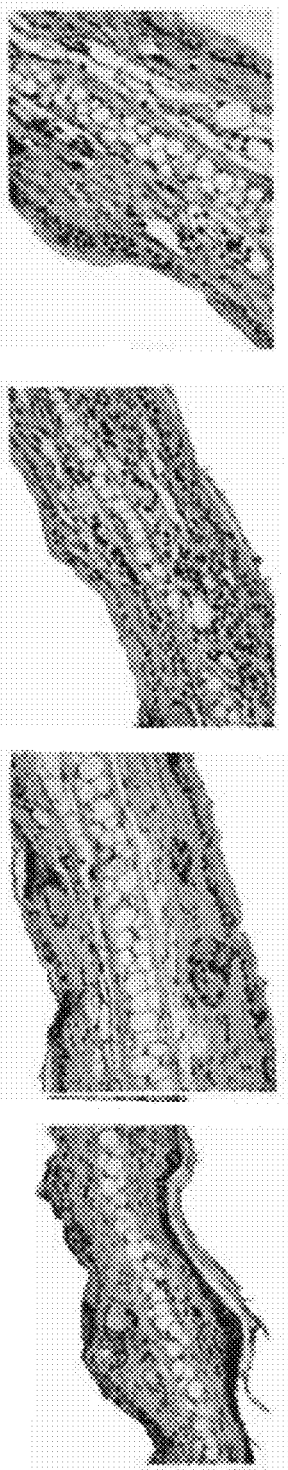
FIGS. 6A-6D show by immunohistochemical examination, the reduction in CFLAR positive cells under various treatment conditions.

Examination of leukocyte infiltration revealed that FITC sensitization alone increased the number of leukocytes in the skin by 37% (p<0.05 versus nonsensitized control ears), while topical application of CFLAR PPMO prior to FITC sensitization reduced these leukocyte numbers to just 5% above nonsensitized controls (p<0.05 versus FITC sensitization alone) (FIG. 5A). The results were generated from histological examination of skin under the various treatment conditions, as shown in FIGS. 5B-5E. CFLAR positive cell distribution within the skin for each treatment group revealed that infiltration of CFLAR positive cells correlated with ear swelling and topical CFLAR PPMO decreased CFLAR positive cells in FITC sensitized ears (FIGS. 6A-6D).

Example 4

Inhibition of Oxazolone-Induced Dermatitis with Topical Application of CFLAR PPMO Contact hypersensitivity responses induced in mice by epicutaneous application of oxazolone were examined to ensure that topical application of CFLAR PPMO could reduce skin inflammation after exposure to antigens other than FITC (see Example 3 above). The delayed-type hypersensitivity (DTH) response was first tested in oxazolone pre-sensitized mice followed by topical administration of 300 µg/ear of CFLAR PPMO (SEQ ID NO: 28), 300 µg/ear scrambled control PPMO (SEQ ID NO: 35), or 95% propylene glycol/5% linoleic acid vehicle (PG/LA) alone to both ears for two days followed immediately by an eliciting dosage of oxazolone applied to each side of one ear (N=6-9 per treatment group). Both ears were measured 24 hours later and the difference between thickness of oxazolone treated and untreated ears for each mouse was determined. The memory response was then tested 15 days later with a second eliciting dose of oxazolone applied to each side of the opposite ear followed by right and left ear thickness measurements five days later. Treatment effectiveness was compared to ears from oxazolone sensitized mice receiving vehicle alone.

Figure 7A:
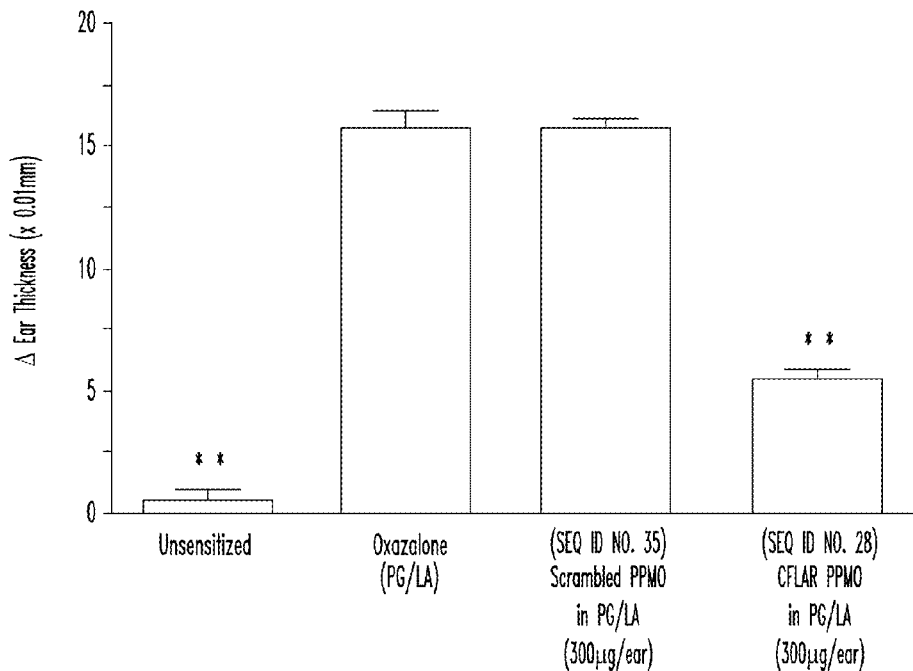
FIGS. 7A and 7B show inhibition of oxazolone-induced dermatitis in mice with topically applied CFLAR PPMO (SEQ ID NO: 28). Topical application of CFLAR PPMO caused inhibition of initial oxazolone-induced delayed-type hypersensitivity (FIG. 7A), and oxazolone-induced memory response at 15 days post initial oxazolone challenge and topical application of CFLAR PPMO (FIG. 7B).

Ear thickness measurements demonstrated that topical CFLAR PPMO reduced oxazolone-induced DTH, with the topical 300 µg/ear dosage causing a 70% decrease in ear thickening (**p<0.001 vs. oxazolone sensitized ears receiving vehicle alone). Topical scrambled control PPMO was no different from vehicle alone (FIG. 7A).

Figure 7B:
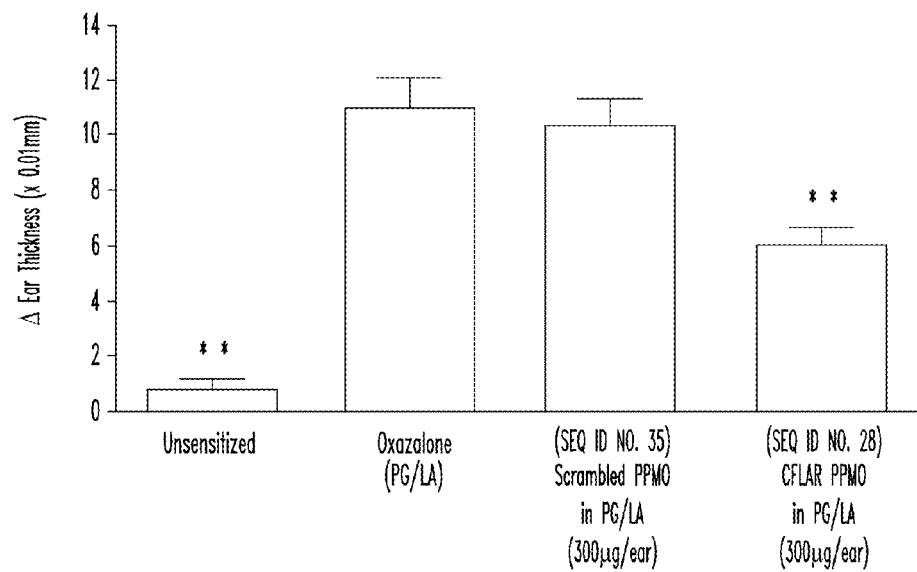

Memory response after the second oxazolone challenge showed that ear thickness was reduced 49% in mice that received topical CFLAR PPMO 15 days earlier (**p<0.001 vs. oxazolone sensitized ears receiving vehicle alone). Topical scrambled control PPMO was again no different from vehicle alone (FIG. 7B).

In summary, the combined results presented in Examples 3 and 4 provide evidence that treatment of skin with topical CFLAR PPMO produced a significant reduction in dermatitis and localized infiltration of lymphocytes that was dose-dependent, target- and antigen-specific, and capable of inducing long-lived tolerance.

SEQUENCE ID LISTING

| Name | Sequences | SEQ ID NO: |
|---|---|---|
| Peptide Transporters (NH$_2$ to COOH) | | |
| rTAT | RRRQRRKKRC | 1 |
| R$_9$F$_2$ | RRRRRRRRRFFC | 2 |
| (RRAhx)$_4$B | RRAhxRRAhxRRAhxRRAhxB | 3 |
| P007 | RAhxRRAhxRRAhxRRAhxRAhxB | 4 |
| (AhxRR)$_4$AhxB | AhxRRAhxRRAhxRRAhxRRAhxB | 5 |
| (RAhx)$_6$B | RAhxRAhxRAhxRAhxRAhxRAhxB | 6 |
| (RAhx)$_8$B | RAhxRAhxRAhxRAhxRAhxRAhxRAhxRAhxB | 7 |
| (RAhxR)$_3$AhxB | RAhxRRAhxRRAhxRAhxB | 8 |
| CP06062 | RAhxRRBRRAhxRRBRAhxB | 9 |
| (RAhxR)$_5$AhxB (CP04057) | RAhxRRAhxRRAhxRRAhxRRAhxRAhxB | 10 |
| Target Sequences (5' to 3') | | |
| Hu-AUG (±30) | CCTTGTGAGCTTCCCTAGTCTAAGAGTAGGATGTCTGCTGAAGTCATCCATCAGGTTGAA | 11 |
| HU-AUG (±12) | TCTAAGAGTAGGATGTCTGCTGAAG | 12 |
| Hu-Ex2SA | CAGAAAAATTCCCTTTTAACCACAG/AACTCCCCCACTGGAAAGGATTCTG | 13 |
| Hu-Ex3SA | CTAAATGAACTTGTCTGGTTTGCAG/AGTGCTGATGGCAGAGATTGGTGAG | 14 |
| Hu-Ex4SA | TGTTTTTTGTTGGTGGTTCTCTTAG/AGTTTCTTGGACCTTGTGGTTGAGT | 15 |
| Hu-Ex2SD | ACCCTCACCTTGTTTCGGACTATAG/GTAATTCATCAACTCTTCCTGAGGC | 16 |
| Hu-Ex3SD | CCGAGGCAAGATAAGCAAGGAGAAG/GTGAGTTTTCTTCTTTTGGTTCATG | 17 |
| Mu-Ex2SA | ATAAGAGGATTCTCTTTCACCACAG/AGTGTCTCTATTGCAAGAACTCTGA | 18 |
| Mu-Ex2SD | ACCCTCACCTGGTTTCTGATTATAG/GTAAGTCATCCCCTGGGGAGGGGA | 19 |
| Mu-Ex3SA | CTGAAGACACTTTTATGGTTTACAG/GGTCCTGCTGATGGAGATTGGTGAG | 20 |
| Mu-Ex3SD | CAGAGGCAAGATAGCCAAGGACAAG/GTGAGTTGTCTTTGCTCGGTGCCTG | 21 |
| Mu-Ex4SA | CATTTCTTGTTCATGGCTTTCTTAG/AGTTTCTTGGATCTGGTGATTGAAT | 22 |
| Oligomer Targeting and Control PMO and PPMO Sequences (5' to 3') | | |
| CFLAR-huAUG1 | CTTCAGCAGACATCCTACTC | 23 |
| CFLAR-huAUG2 | GACTAGGGAAGCTCACAAGG | 24 |
| CFLAR-huAUG3 | TCAACCTGATGGATGACTTC | 25 |
| CFLAR-huAUG (-5) | GATGACTTCAGCAGACATCCTAC | 26 |
| CFLAR-huAUG (-11) | CTTCAGCAGACATCCTACTCTTAG | 27 |

| Name | Sequences | SEQ ID NO: |
|---|---|---|
| CFLAR-muAUG | CTGGGCCATGTTCAGAACC | 28 |
| CFLAR-huSA2 | GGAGTTCTGTGGTTAAAAGG | 29 |
| CFLAR-huSD2 | CTATAGTCCGAAACAAGGTGAGG | 30 |
| CFLAR-huSA3 | CACCAATCTCTGCCATCAGCACT | 31 |
| CFLAR-huSA4 | TCAACCACAAGGTCCAAGAAACT | 32 |
| CFLAR-huSD3 | CTTCTCCTTGCTTATCTTGCCCT | 33 |
| R$_9$F$_2$-CFLARmuAUG; CFLAR PPMO | RRRRRRRRRFFC-CTGGGCCATGTTCAGAACC | 34 |
| Scrambled Control | TGCGCGTCATGTACGCCAA | 35 |
| R$_9$F$_2$-Scr. Control; Scrambled Control PPMO | RRRRRRRRRFFC-TGCGCGTCATGTACGCCAA | 36 |

It is claimed:

1. A method of reducing contact hypersensitivity or contact dermatitis, comprising contacting the skin or mucous membrane of a subject with a sensitizing agent and an effective amount of an antisense composition containing an antisense oligonucleotide, wherein the sensitizing agent is a hapten or a metal ion complexed with a protein, wherein the oligonucleotide contains between 12-40 nucleotide bases, and a base sequence effective to hybridize to at least 12 contiguous bases of a target sequence contained within SEQ ID NO:11, wherein the oligonucleotide binding to the target sequence is effective to reduce expression of a functional human CFLAR in CFLAR-expressing lymphocytes, and thereby reducing contact hypersensitivity or contact dermatitis in the subject.

2. A method of reducing contact hypersensitivity or contact dermatitis, comprising contacting the skin or mucous membrane of a subject with a sensitizing agent and an effective amount of an antisense composition containing an antisense oligonucleotide, wherein the sensitizing agent is an acid, an alkali, a solvent, a heavy metal, a rubber, latex, a surfactant, kerosene, chlorine, ethylene oxide, a cosmetic, an antiseptic, an insecticide, potassium dichromate, paraphenylenediamine, a dental product, formaldehyde, a fragrance, urushiol oil, an antibiotic, a topical steroid, a fungicide, or quaternium-15, wherein the oligonucleotide contains between 12-40 nucleotide bases, and a base sequence effective to hybridize to at least 12 contiguous bases of a target sequence contained within SEQ ID NO:11, wherein the oligonucleotide binding to the target sequence is effective to reduce expression of a functional human CFLAR in CFLAR-expressing lymphocytes, and thereby reducing contact hypersensitivity or contact dermatitis in the subject.

3. The method of claim 1, wherein the oligonucleotide is a peptide nucleic acid (PNA), a locked nucleic acid (LNA), an RNA interference agent with a duplex region, or a morpholino oligonucleotide.

4. The method of claim 3, wherein the morpholino oligonucleotide contains morpholino subunits that are joined by phosphorodiamidate linkages, in accordance with the structure:

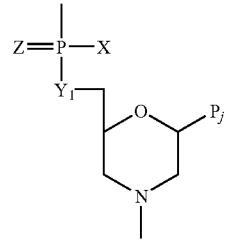

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino e.g., wherein X=$NR_2$, where each R is independently hydrogen or methyl.

5. The method of claim 3, wherein the intersubunit linkages are interspersed with linkages that are positively charged at physiological pH, where the total number of positively charged linkages is between 2 and no more than half of the total number of linkages.

6. The method of claim 5, wherein the positively charged linkages have a phosphorodiamidate structure in which X is 1-piperazine.

7. The method of claim 1, wherein the composition comprises a carrier or delivery vehicle for contacting the skin or mucous membrane.

8. The method of claim 7, wherein the carrier or delivery vehicle includes propylene glycol, an acyl-chain lipid, or both.

9. The method of claim 2, wherein the oligonucleotide is a peptide nucleic acid (PNA), a locked nucleic acid (LNA), an RNA interference agent with a duplex region, or a morpholino oligonucleotide.

10. The method of claim 9, wherein the morpholino oligonucleotide contains morpholino subunits that are joined by phosphorodiamidate linkages, in accordance with the structure:

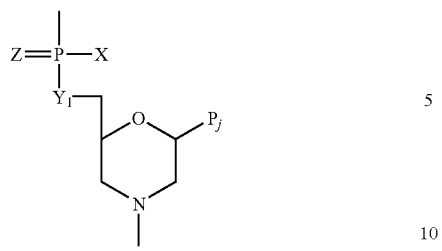

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino e.g., wherein X=$NR_2$, where each R is independently hydrogen or methyl.

11. The method of claim 9, wherein the intersubunit linkages are interspersed with linkages that are positively charged at physiological pH, where the total number of positively charged linkages is between 2 and no more than half of the total number of linkages.

12. The method of claim 11, wherein the positively charged linkages have a phosphorodiamidate structure in which X is 1-piperazine.

13. The method of claim 2, wherein the composition comprises a carrier or delivery vehicle for contacting the skin or mucous membrane.

14. The method of claim 13, wherein the carrier or delivery vehicle includes propylene glycol, an acyl-chain lipid, or both.

* * * * *

SEQUENCE LISTING

```
<160> NUMBER OF SEQ ID NOS: 39

<210> SEQ ID NO 1
<211> LENGTH: 10
<212> TYPE: PRT
<213> ORGANISM: Artificial Sequence
<220> FEATURE:
<223> OTHER INFORMATION: Tranport peptide for cellular uptake
      enhancement

<400> SEQUENCE: 1

Arg Arg Arg Gln Arg Arg Lys Lys Arg Cys
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Tranport peptide for cellular uptake
      enhancement

<400> SEQUENCE: 2

Arg Arg Arg Arg Arg Arg Arg Arg Arg Phe Phe Cys
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 3, 6, 9, 12
<223> OTHER INFORMATION: Xaa = 6-aminohexanoic acid
<220> FEATURE:
<221> NAME/KEY: MOD_RES
<222> LOCATION: 13
<223> OTHER INFORMATION: Xaa = beta alanine

<400> SEQUENCE: 3

Arg Arg Xaa Arg Arg Xaa Arg Arg Xaa Arg Arg Xaa Xaa
 1               5                  10

<210> SEQ ID NO 4
```

```
<211> LENGTH: 14
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 2, 5, 8, 11, 13
<223> OTHER INFORMATION: Xaa = 6-aminohexanoic acid
<220> FEATURE:
<221> NAME/KEY: MOD_RES
<222> LOCATION: 14
<223> OTHER INFORMATION: Xaa = beta alanine

<400> SEQUENCE: 4

Arg Xaa Arg Arg Xaa Arg Arg Xaa Arg Arg Xaa Arg Xaa Xaa
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 1, 4, 7, 10, 13
<223> OTHER INFORMATION: Xaa = 6-aminohexanoic acid
<220> FEATURE:
<221> NAME/KEY: MOD_RES
<222> LOCATION: 14
<223> OTHER INFORMATION: Xaa = beta alanine

<400> SEQUENCE: 5

Xaa Arg Arg Xaa Arg Arg Xaa Arg Arg Xaa Arg Arg Xaa Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 2, 4, 6, 8, 10, 12
<223> OTHER INFORMATION: Xaa = 6-aminohexanoic acid
<220> FEATURE:
<221> NAME/KEY: MOD_RES
<222> LOCATION: 13
<223> OTHER INFORMATION: Xaa = beta alanine

<400> SEQUENCE: 6

Arg Xaa Arg Xaa Arg Xaa Arg Xaa Arg Xaa Arg Xaa Xaa
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 2, 4, 6, 8, 10, 12, 14, 16
<223> OTHER INFORMATION: Xaa = 6-aminohexanoic acid
<220> FEATURE:
<221> NAME/KEY: MOD_RES
<222> LOCATION: 17
<223> OTHER INFORMATION: Xaa = beta alanine
```

<400> SEQUENCE: 7

Arg Xaa Arg Xaa Arg Xaa Arg Xaa Arg Xaa Arg Xaa Arg Xaa Arg Xaa
1               5                   10                  15

Xaa

<210> SEQ ID NO 8
<211> LENGTH: 11
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 2, 5, 8, 10
<223> OTHER INFORMATION: Xaa = 6-aminohexanoic acid
<220> FEATURE:
<221> NAME/KEY: MOD_RES
<222> LOCATION: 11
<223> OTHER INFORMATION: Xaa = beta alanine

<400> SEQUENCE: 8

Arg Xaa Arg Arg Xaa Arg Arg Xaa Arg Xaa Xaa
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 2, 8, 13
<223> OTHER INFORMATION: Xaa = 6-aminohexanoic acid
<220> FEATURE:
<221> NAME/KEY: MOD_RES
<222> LOCATION: 5, 11, 14
<223> OTHER INFORMATION: Xaa = beta alanine

<400> SEQUENCE: 9

Arg Xaa Arg Arg Xaa Arg Arg Xaa Arg Arg Xaa Arg Xaa Xaa
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 2, 5, 8, 11, 14, 16
<223> OTHER INFORMATION: Xaa = aminohexanoic acid
<220> FEATURE:
<221> NAME/KEY: MOD_RES
<222> LOCATION: 17
<223> OTHER INFORMATION: Xaa = beta alanine

<400> SEQUENCE: 10

Arg Xaa Arg Arg Xaa Arg Arg Xaa Arg Arg Xaa Arg Arg Xaa Arg Xaa
1               5                   10                  15

Xaa

<210> SEQ ID NO 11
<211> LENGTH: 60
<212> TYPE: DNA

<213> ORGANISM: Homo sapiens

<400> SEQUENCE: 11
ccttgtgagc ttccctagtc taagagtagg atgtctgctg aagtcatcca tcaggttgaa    60

<210> SEQ ID NO 12
<211> LENGTH: 25
<212> TYPE: DNA
<213> ORGANISM: Homo sapiens

<400> SEQUENCE: 12
tctaagagta ggatgtctgc tgaag    25

<210> SEQ ID NO 13
<211> LENGTH: 50
<212> TYPE: DNA
<213> ORGANISM: Homo sapiens

<400> SEQUENCE: 13
cagaaaaatt cccttttaac cacagaactc ccccactgga aaggattctg    50

<210> SEQ ID NO 14
<211> LENGTH: 50
<212> TYPE: DNA
<213> ORGANISM: Homo sapiens

<400> SEQUENCE: 14
ctaaatgaac ttgtctggtt tgcagagtgc tgatggcaga gattggtgag    50

<210> SEQ ID NO 15
<211> LENGTH: 50
<212> TYPE: DNA
<213> ORGANISM: Homo sapiens

<400> SEQUENCE: 15
tgttttttgt tggtggttct cttagagttt cttggacctt gtggttgagt    50

<210> SEQ ID NO 16
<211> LENGTH: 50
<212> TYPE: DNA
<213> ORGANISM: Homo sapiens

<400> SEQUENCE: 16
accctcacct tgtttcggac tataggtaat tcatcaactc ttcctgaggc    50

<210> SEQ ID NO 17
<211> LENGTH: 50
<212> TYPE: DNA
<213> ORGANISM: Homo sapiens

<400> SEQUENCE: 17
ccgaggcaag ataagcaagg agaaggtgag ttttcttctt ttggttcatg    50

<210> SEQ ID NO 18
<211> LENGTH: 50
<212> TYPE: DNA
<213> ORGANISM: Mus musculus

<400> SEQUENCE: 18
ataagaggat tctctttcac cacagagtgt ctctattgca agaactctga    50

<210> SEQ ID NO 19
<211> LENGTH: 50
<212> TYPE: DNA

<213> ORGANISM: Mus musculus

<400> SEQUENCE: 19
accctcacct ggtttctgat tataggtaag tcatcccctg ggggagggga            50

<210> SEQ ID NO 20
<211> LENGTH: 50
<212> TYPE: DNA
<213> ORGANISM: Mus musculus

<400> SEQUENCE: 20
ctgaagacac ttttatggtt tacagggtcc tgctgatgga gattggtgag            50

<210> SEQ ID NO 21
<211> LENGTH: 50
<212> TYPE: DNA
<213> ORGANISM: Mus musculus

<400> SEQUENCE: 21
cagaggcaag atagccaagg acaaggtgag ttgtctttgc tcggtgcctg            50

<210> SEQ ID NO 22
<211> LENGTH: 50
<212> TYPE: DNA
<213> ORGANISM: Mus musculus

<400> SEQUENCE: 22
catttcttgt tcatggcttt cttagagttt cttggatctg gtgattgaat            50

<210> SEQ ID NO 23
<211> LENGTH: 20
<212> TYPE: DNA
<213> ORGANISM: Artificial Sequence
<220> FEATURE:
<223> OTHER INFORMATION: Human CFLAR antisense targeting sequence

<400> SEQUENCE: 23
cttcagcaga catcctactc                                             20

<210> SEQ ID NO 24
<211> LENGTH: 20
<212> TYPE: DNA
<213> ORGANISM: Artificial Sequence
<220> FEATURE:
<223> OTHER INFORMATION: Human CFLAR antisense targeting sequence

<400> SEQUENCE: 24
gactagggaa gctcacaagg                                             20

<210> SEQ ID NO 25
<211> LENGTH: 20
<212> TYPE: DNA
<213> ORGANISM: Artificial Sequence
<220> FEATURE:
<223> OTHER INFORMATION: Human CFLAR antisense targeting sequence

<400> SEQUENCE: 25
tcaacctgat ggatgacttc                                             20

<210> SEQ ID NO 26
<211> LENGTH: 23
<212> TYPE: DNA
<213> ORGANISM: Artificial Sequence
<220> FEATURE:
<223> OTHER INFORMATION: Human CFLAR antisense targeting sequence

```
<400> SEQUENCE: 26
gatgacttca gcagacatcc tac                                             23

<210> SEQ ID NO 27
<211> LENGTH: 24
<212> TYPE: DNA
<213> ORGANISM: Artificial Sequence
<220> FEATURE:
<223> OTHER INFORMATION: Human CFLAR antisense targeting sequence

<400> SEQUENCE: 27
cttcagcaga catcctactc ttag                                            24

<210> SEQ ID NO 28
<211> LENGTH: 19
<212> TYPE: DNA
<213> ORGANISM: Artificial Sequence
<220> FEATURE:
<223> OTHER INFORMATION: Murine CFLAR antisense targeting sequence

<400> SEQUENCE: 28
ctgggccatg ttcagaacc                                                  19

<210> SEQ ID NO 29
<211> LENGTH: 20
<212> TYPE: DNA
<213> ORGANISM: Artificial Sequence
<220> FEATURE:
<223> OTHER INFORMATION: Human CFLAR antisense targeting sequence

<400> SEQUENCE: 29
ggagttctgt ggttaaaagg                                                 20

<210> SEQ ID NO 30
<211> LENGTH: 23
<212> TYPE: DNA
<213> ORGANISM: Artificial Sequence
<220> FEATURE:
<223> OTHER INFORMATION: Human CFLAR antisense targeting sequence

<400> SEQUENCE: 30
ctatagtccg aaacaaggtg agg                                             23

<210> SEQ ID NO 31
<211> LENGTH: 23
<212> TYPE: DNA
<213> ORGANISM: Artificial Sequence
<220> FEATURE:
<223> OTHER INFORMATION: Human CFLAR antisense targeting sequence

<400> SEQUENCE: 31
caccaatctc tgccatcagc act                                             23

<210> SEQ ID NO 32
<211> LENGTH: 23
<212> TYPE: DNA
<213> ORGANISM: Artificial Sequence
<220> FEATURE:
<223> OTHER INFORMATION: Human CFLAR antisense targeting sequence

<400> SEQUENCE: 32
tcaaccacaa ggtccaagaa act                                             23

<210> SEQ ID NO 33
<211> LENGTH: 22
<212> TYPE: DNA
```

```
<213> ORGANISM: Artificial Sequence
<220> FEATURE:
<223> OTHER INFORMATION: Human CFLAR antisense targeting sequence

<400> SEQUENCE: 33
cttctccttg cttatcttgc ct                                              22

<210> SEQ ID NO 34

<400> SEQUENCE: 34

000

<210> SEQ ID NO 35
<211> LENGTH: 19
<212> TYPE: DNA
<213> ORGANISM: Artificial Sequence
<220> FEATURE:
<223> OTHER INFORMATION: Control CFLAR antisense targeting sequence

<400> SEQUENCE: 35
tgcgcgtcat gtacgccaa                                                  19

<210> SEQ ID NO 36

<400> SEQUENCE: 36

000

<210> SEQ ID NO 37
<211> LENGTH: 12
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 1, 3, 4, 7, 9, 10
<223> OTHER INFORMATION: Xaa = Lysine, Arginine or Arginine analog
<220> FEATURE:
<221> NAME/KEY: MOD_RES
<222> LOCATION: 2, 8
<223> OTHER INFORMATION: Xaa = a neutral amino acid
<220> FEATURE:
<221> NAME/KEY: MOD_RES
<222> LOCATION: 5, 6, 11, 12
<223> OTHER INFORMATION: Xaa = a neutral alpha amino acid having a
      neutral aralkyl side chain

<400> SEQUENCE: 37

Xaa Xaa Xaa Xaa Xaa Xaa Xaa Xaa Xaa Xaa Xaa Xaa
 1               5                  10

<210> SEQ ID NO 38
<211> LENGTH: 12
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 2, 6, 8, 12
<223> OTHER INFORMATION: Xaa = 6-aminohexanoic acid

<400> SEQUENCE: 38

Arg Xaa Arg Arg Arg Xaa Arg Xaa Arg Arg Arg Xaa
 1               5                  10
```

```
<210> SEQ ID NO 39
<211> LENGTH: 9
<212> TYPE: PRT
<213> ORGANISM: Artificial Sequence
<220> FEATURE:
<223> OTHER INFORMATION: Tranport peptide for cellular uptake
      enhancement
<220> FEATURE:
<221> NAME/KEY: MOD_RES
<222> LOCATION: 3, 5, 9
<223> OTHER INFORMATION: Xaa = 6-aminohexanoic acid

<400> SEQUENCE: 39

Arg Arg Xaa Arg Xaa Arg Arg Arg Xaa
 1               5
```